US007776612B2

United States Patent
Kawai et al.

(10) Patent No.: US 7,776,612 B2
(45) Date of Patent: Aug. 17, 2010

(54) METHOD OF QUANTIFYING ANTIGEN EXPRESSION

(75) Inventors: Shigeto Kawai, Gotenba (JP); Shinichiro Iida, Gotenba (JP); Yasuo Koishihara, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1233 days.

(21) Appl. No.: 10/474,714

(22) PCT Filed: Apr. 12, 2002

(86) PCT No.: PCT/JP02/03703

§ 371 (c)(1),
(2), (4) Date: Oct. 10, 2003

(87) PCT Pub. No.: WO02/084290

PCT Pub. Date: Oct. 24, 2002

(65) Prior Publication Data

US 2004/0115741 A1  Jun. 17, 2004

(30) Foreign Application Priority Data

Apr. 13, 2001  (JP) ................ 2001-115889

(51) Int. Cl.
*G01N 21/76* (2006.01)
(52) U.S. Cl. .............. 436/172; 435/7.2; 435/7.23; 435/7.24; 435/287.1; 436/545; 436/546; 436/10; 436/55; 436/56; 436/63; 436/64; 436/164; 422/61; 422/73; 422/82.08
(58) Field of Classification Search ............. 435/2, 435/3, 344, 6, 7.23, 7.24, 372, 7.92, 40.5, 435/328, 343.1, 343.2, 7.2, 287.1; 436/513, 436/545, 546, 10, 55, 56, 64, 172, 63, 164; 422/61, 73, 82.08; 530/387.3, 388.1
See application file for complete search history.

(56) References Cited

U.S. PATENT DOCUMENTS 4,444,879 A * 4/1984 Foster et al. ............... 435/7.95

FOREIGN PATENT DOCUMENTS

| EP | 0 960 936 A1 | 12/1999 |
| EP | 1 023 906 A1 | 8/2000 |
| EP | 1 025 522 | 8/2000 |
| EP | 1 059 533 A1 | 12/2000 |
| JP | 61-223559 A | 10/1986 |
| JP | 63-036151 A | 2/1988 |
| JP | 09-196916 A | 7/1997 |
| JP | 10-155494 A | 6/1998 |
| JP | 10-286088 A | 10/1998 |
| WO | WO 00/17395 A1 | 3/2000 |

OTHER PUBLICATIONS

Ono et al., The humanized anti-HM1.24 antibody effectively kills multiple myeloma cells by human effector cell-mediated cytotoxicity, Molecular Immunology 36: 387-395 (1999).*
By Ozaki et al., Humanized Anti-HM1.24 Antibody Mediates Myeloma Cell Cytotoxicity That Is Enhanced by Cytokine Stimulation of Effector Cells, Blood 93 (11): 3922-3928 (1999).*
Okayama et al. (Expression of Functional High-Affinity IgG Receptor, FcγRI, On Human Mast Cells:Upregulation by IFN-γ, The Journal of Immunology 164: 4332-4339 (2000)).*
Keiji Ozaki et al., "Localization and Imaging of Human Plasmacytoma Xenografts in Severe Combined Immunodeficiency Mice by a New Murine Monoclonal Antibody, Anti-HMI.24", Journal of Experimental Medicine, vol. 43, 1996, pp. 7-15.
Tetsuya Goto et al., "Novel Membrane Antigen Selectively Expressed on Terminally Differentiated Human B Cells", Blood, vol. 84, No. 6, Sep. 15, 1994, pp. 1922-1930.
Shuji Ozaki et al., "Immunotherapy of Multiple Myeloma With a Monoclonal Antibody Directed Against a Plasma Cell-Specific Antigen, HM1.24", Blood, vol. 90, No. 8, Oct. 15, 1997, pp. 3179-3188.
Koichiro Ono et al., "The Humanized Anti-HM1.24 Antibody Effectively Kills Multiple Myeloma Cells by Human Effector Cell-Mediated Cytotoxicity", Molecular Immunology, vol. 36, No. 6, Apr. 1999, pp. 387-395.
Toshihiko Ohtomo et al., "Molecular Cloning and Characterization of a Surface Antigen Preferentially Overexpressed on Multiple Myeloma Cells", Biochemical and Biophysical Research Communicaitons, vol. 258, No. 3, 1999, pp. 583-591.
Shuji Ozaki et al., "Humanized Anti-HM1.24 Antibody Mediates Myeloma Cell Cytotoxicity That Is Enhanced by Cytokine Stimulation of Effector Cells", Blood, vol. 93, No. 11, Jun. 1, 1999, pp. 3922-3930.
Ozaki et al., The Japanese Journal of Clinical Hematology, 2000, 41(10):989.

* cited by examiner

*Primary Examiner*—Gailene R Gabel
(74) *Attorney, Agent, or Firm*—Foley & Lardner LLP

(57) ABSTRACT

The present invention is directed to a novel method for quantifying antigen, such as the amount expressed on a cell. The method comprises formulating an equation of correlation between the amount expressed of expressed antigen and the intensity of fluorescence from fluorescent labelled antibody.

11 Claims, 20 Drawing Sheets

METHOD OF QUANTIFYING ANTIGEN EXPRESSION

FIELD OF THE INVENTION

The present invention relates to a method of determining an amount of expressed antigen and the uses thereof.

BACKGROUND ART

Goto, T. et al. have reported a monoclonal antibody (mouse anti-HM1.24 antibody) that was obtained by immunizing human plasma cells and that specifically recognizes an antigen with a molecular weight of 29-33 kDa specifically expressed in B cell lines (Blood (1994) 84, 1922-1930). The antigen recognized by mouse anti-HM1.24 antibody is referred to as HM1.24 antigen. When anti-HM1.24 antibody was administered to a mouse transplanted with human myeloma cells, the antibody accumulated in tumor tissues in a specific manner (Masaaki Kosaka et al., Nippon Rinsho (Japan Clinical) (1995) 53, 627-635), suggesting that anti-HM1.24 antibody could be applied in the diagnosis of tumor localization by radioisotopic labeling, missile therapies such as radiotherapy, and the like.

In the above Blood (1994) 84, 1922-1930, it has been described that anti-HM1.24 antibody has an in vitro cytotoxic activity on a human myeloma cell line RPMI8226. There have also been prepared a chimeric anti-HM1.24 antibody in which the constant region of a mouse anti-HM1.24 antibody has been replaced with a human constant region and a humanized anti-HM1.24 antibody (reshaped anti-HM1.24 antibody) in which the complementarity determining region (CDR) of a mouse anti-HM1.24 antibody has been grafted to a human antibody and some FR amino acids have been replaced (WO 98/14580). It has also been shown that chimeric anti-HM1.24 antibody and a humanized anti-HM1.24 antibody specifically bind to myeloma cells and have a cytotoxic activity (Blood (1999) 93, 3922-3930).

On the other hand, it has also been demonstrated for lymphatic tumors that an antigen protein (HM1.24 antigen) recognized by anti-HM1.24 antibody is expressed in lymphatic tumors and that anti-HM1.24 antibody has a cytotoxic activity on lymphatic tumors due to a complement-dependent cytotoxicity (CDC activity) and an antibody-dependent cellular cytotoxicity (ADCC activity), and thereby exhibits anti-tumor effect (WO 98/35698).

Thus, HM1.24 antigen has been highly expressed in a specific manner not only on myeloma cells that are terminally differentiated B cells but also in lymphatic tumors, and the anti-HM1.24 antibody, in particular humanized anti-HM1.24 antibody, that recognizes HM1.24 antigen, is useful as a therapeutic agent for myeloma including multiple myeloma and lymphatic tumors.

As anti-HM1.24 antibody binds to HM1.24 antigen expressed on the surface of target cells and exhibits cell-killing activity through the CDC activity and the ADCC activity, said activities depend on the amount of HM1.24 antigen expressed on the surface of target cells. Thus, if the amount of HM1.24 antigen expressed on tumor cells of subject patients could be determined when predicting the effect of anti-HM1.24 antibody, in particular humanized anti-HM1.24 antibody, on patients with multiple myeloma or patients with lymphatic tumors, precise prediction of therapeutic effects would become possible.

DISCLOSURE OF THE INVENTION

Generally, flow cytometry has been widely used as a method of determining qualitatively the amount of antigen present on the cell surface. Flow cytometry can simply determine the amount expressed of a molecule on the cell as the intensity of fluorescence. The fluorescence intensity is a relative amount, however, and it is impossible to compare directly data on fluorescence intensity obtained at different times or with different instruments. Thus, in order to quantitate the amount expressed of HM1.24 antigen using a fluorescence-labelled anti-HM1.24 antibody, the fluorescence intensity obtained must be standardized.

Means to Solve the Problems

After intensive and extensive research, the present inventors have found a method of quantitating the amount of antigen expressed in the cell using a fluorescence-labelled antibody. Also, the inventors have also found a method of formulating an equation of correlation between fluorescence intensity due to the fluorescence-labelled antibody and the amount expressed of antigen. By using these methods, it has become possible to diagnose patients and predict sensitivity to drug therapy. More specifically, test cells were reacted with the desired antigen-specific antibody labelled with fluorescein or a fluorescein-labelled control antibody, the fluorescence intensity thereof was measured by a flow cytometer, and using a standard curve obtained using the SPHERO (™) Rainbow Calibration Particles the fluorescence intensity of the cells was standardized as a Log MEFL value.

Furthermore, by preparing beads to which a given amount of antigen was bound, and using the beads as a positive control, the standardization of the assay system and reagents and the implementation of quality control has become possible. In fact, when a humanized anti-HM1.24 antibody was used to determine six hematologic tumor cell lines (RPMI8226, U266Bl, ARH-77, KPMM2, IM-9, HS-Sultan), peripheral blood mononuclear cells, and tumor cells derived from five patients with myeloma, the expression of HM1.24 antigen was confirmed in all the cells, and the amount expressed thereof could be quantitated. Furthermore, correlation between the Log MEFL value and the amount expressed of HM1.24 antigen and between the Log MEFL value and the ADCC activity due to humanized anti-HM1.24 antibody was investigated.

As a result, it was revealed that there is a high correlation between the amount expressed of HM1.24 antigen and the Log MEFL value with a correlation coefficient of 0.9936. Also, when the ADCC activity of humanized anti-HM1.24 antibody via human peripheral blood mononuclear cells was determined using these cells as target cells, ADCC activity corresponding to the amount of HM1.24 antigen expressed on the target cells was induced, demonstrating that it is possible to predict the responsiveness of patients to humanized anti-HM1.24 antibody. Therefore, the present invention is a method of formulating the equation of correlation between the amount expressed of the desired antigen and fluorescence intensity, comprising the steps of:

(a) preparing a plurality of cell groups for which the amount expressed of said antigen has previously quantitated;

(b) preparing a fluorescence-labelled antibody that specifically binds to said antigen;

(c) determining the fluorescence intensity for each of the cell groups of (a) using the fluorescence-labelled antibody of (b); and (d) analyzing the correlation between the amount expressed of the previously quantitated antigen and the fluorescence intensity determined in (c).

In the above method, the step of preparing a plurality of cell groups for which the amount expressed of said antigen has previously been quantitated comprises the steps of preparing a plurality of cell groups for which the amounts expressed of said antigen are different, and of quantitating the amount expressed of said antigen using an antibody labelled with a radioisotope. The plurality of cell groups for which the amounts expressed of said antigen are different are a plurality of cell groups for which the amounts expressed of said antigen are different by at least ten times or more.

The present invention is also a method of determining the amount of the desired antigen expressed in test cells, comprising the steps of:

(a) preparing a fluorescence-labelled antibody that specifically binds to said antigen;

(b) preparing an equation of correlation between the amount expressed of said antigen and fluorescence intensity due to the fluorescence-labelled antibody of (a);

(c) contacting the test cells with the fluorescence-labelled antibody of (a) and then determining the fluorescence intensity of said cells; and (d) calculating the amount of said antigen expressed in the test cells from the fluorescence intensity determined in the above (c) using the equation of correlation of (b).

In the above method, an equation of correlation between the amount expressed of said antigen and fluorescence intensity due to the fluorescence-labelled antibody of (a) may be obtained by the above formulating method.

Also, the present invention is a method of formulating an equation of correlation between the desired drug therapy and the sensitivity of patients to said drug therapy, comprising the steps of:

(a) selecting a group of subject patients;

(b) selecting an antigen which is expected to affect the sensitivity of the patients to said drug therapy;

(c) preparing a fluorescence-labelled antibody that specifically binds to said antigen;

(d) preparing an equation of correlation between the amount expressed of said antigen and fluorescence intensity due to the fluorescence-labelled antibody of (c);

(e) contacting the test cells derived from the subject patients with the fluorescence-labelled antibody of (c), and then determining the fluorescence intensity of said cells;

(f) calculating the amount of said antigen expressed in the test cells from the fluorescence intensity determined in the above (e) using the equation of correlation of (d); and (g) comparing the amount expressed of said antigen calculated from the above (f) with the effect on the drug therapy of the patients to analyze correlation.

The present invention provides a method of predicting the sensitivity of patients to the desired drug therapy, comprising the steps of:

(a) selecting an antigen of which the amount expressed is specifically increased in a disease;

(b) preparing a fluorescence-labelled antibody that specifically binds to said antigen;

(c) preparing an equation of correlation between the amount expressed of said antigen and fluorescence intensity due to the fluorescence-labelled antibody of (b);

(d) contacting the test cells derived from the patients with the fluorescence-labelled antibody of (b) and then determining the fluorescence intensity of said cells;

(e) calculating the amount of said antigen expressed in the test cells from the fluorescence intensity determined in the above (d) using the equation of correlation of (c); and (f) comparing the amount expressed of said antigen calculated from the above (e) with the correlation of sensitivity of the patients to said drug therapy.

The present invention further provides a method of diagnosing patients and/or identifying diseases, comprising the steps of:

(a) selecting an antigen of which the amount expressed is specifically increased in a disease;

(b) preparing a fluorescence-labelled antibody that specifically binds to said antigen;

(c) preparing an equation of correlation between the amount expressed of said antigen and fluorescence intensity due to the fluorescence-labelled antibody of (b);

(d) contacting the test cells derived from the patients with the fluorescence-labelled antibody of (b), and then determining the fluorescence intensity of said cells;

(e) calculating the amount of said antigen expressed in the test cells from the fluorescence intensity determined in the above (d) using the equation of correlation of (c); and (f) comparing the amount expressed of said antigen calculated from the above (e) with the amount expressed of said antigen for normal healthy humans.

The present invention also provides a kit comprising a pharmaceutical composition containing an antibody as an active ingredient and an instruction manual describing the correlation of patient's sensitivity to said antibody and/or said pharmaceutical composition.

In the kit, the antibody is preferably an antibody having an ADCC activity and/or a CDC activity. The pharmaceutical composition comprising said antibody as an active ingredient is, for example, a pharmaceutical composition comprising anti-HM1.24 antibody as an active ingredient for the treatment of hematopoietic tumors. Said hematopoietic tumors represent, for example, myeloma and/or lymphatic tumors. Said myeloma is, for example, multiple myeloma. Correlation of patient's sensitivity to said antibody and/or said pharmaceutical composition is useful in cases where there is an amount expressed of antigen greater than a given amount per cell in the test cells derived from patients.

The present invention further provides a pharmaceutical composition that comprises an antibody as an active ingredient and that is administered to the patients when the amount expressed of the antigen expressed on the test cells derived from the patient is greater than a given amount. Said antibody is an antibody having an ADCC activity and/or a CDC activity. Said pharmaceutical composition is, for example, a pharmaceutical composition comprising anti-HM1.24 antibody as an active ingredient for the treatment of hematopoietic tumors. Said hematopoietic tumors represent, for example, myeloma and/or lymphatic tumors. Said myeloma is, for example, multiple myeloma.

BEST MODE FOR CARRYING OUT THE INVENTION

Figure 1:
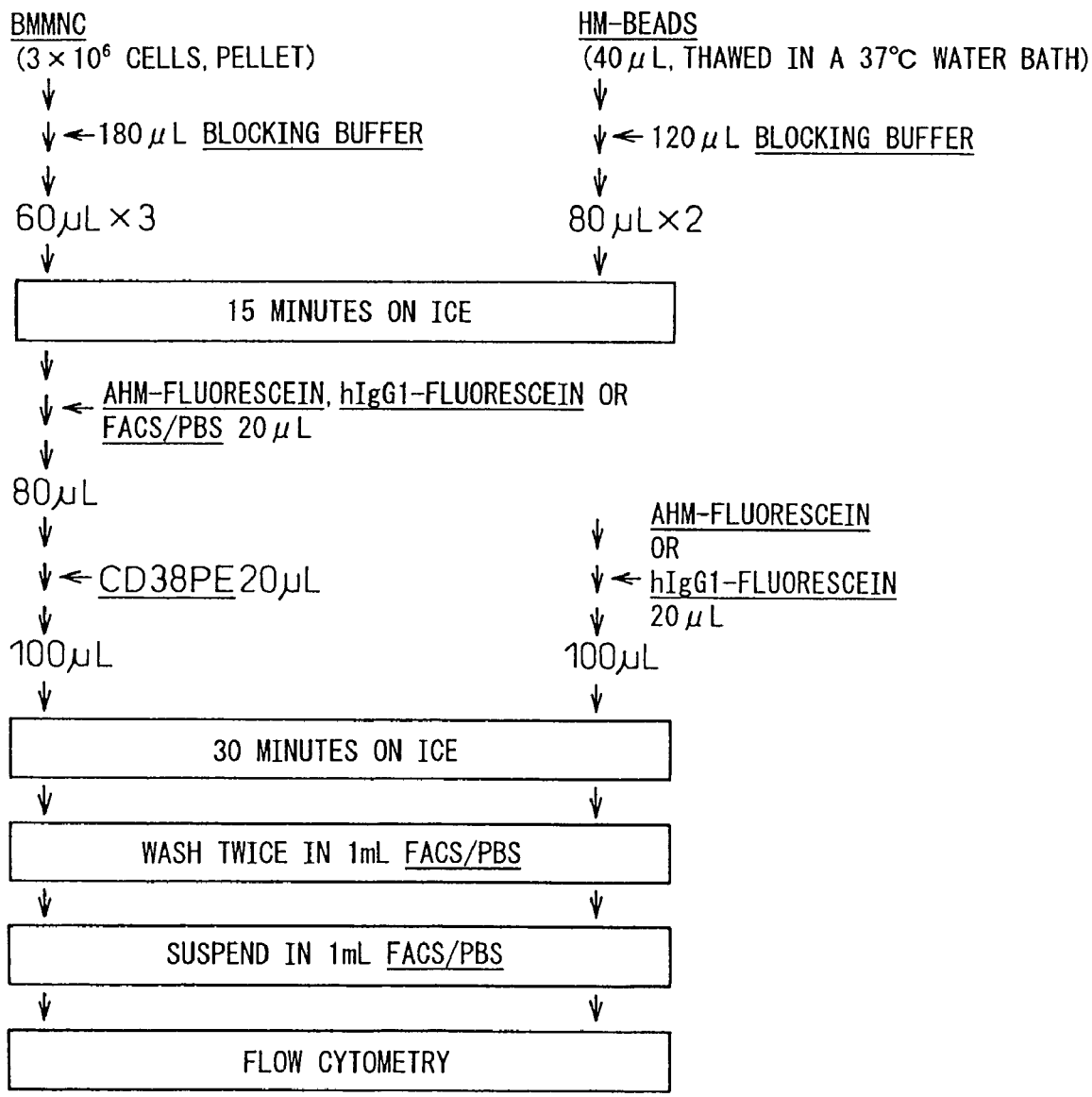
FIG. 1 is a schematic illustration of a method of staining human bone marrow-derived mononuclear cells (BMMNC).

The method of the present invention can be used for any molecules having antigenicity. Antigenicity means a characteristics of having a site recognized by the antibody or a characteristic of having a site where the antibody binds. In other words, it is a molecule having an epitope. The antigen for use in the present invention need not have immunogenicity. Immunogenicity is a characteristics that induces the production of specific antibody in a living body.

Thus, the antigen for use in the present invention is a molecule that has at least antigenicity, and though it may or may not have immunogenicity, the antigen preferably has immunogenicity since it facilitates the production of antibody against the antigen. Even when the antigen has no immunogenicity, a specific antibody against the antigen can be obtained by preparing a complex of the antigen with a molecule having immunogenicity and then by using said complex for immunization. As molecules having immunogenicity, a protein of an animal species different from the animal to be immunized can be used, for example human albumin or rat albumin can be used when a mouse is to be immunized.

The antigen for use in the present invention may be of any type as long as it has a site (epitope) to be recognized by an antibody, and may be a protein, a sugar chain, a polynucleotide, an oligonucleotide, a glycoprotein, a proteoglycan, or an organic compound. The Polynucleotide includes DNA and RNA. The organic compound is any molecule that has carbon, hydrogen, and oxygen as major constituent atoms, and do not have amino acids or nucleic acids as building blocks, and preferably is a molecule having a molecular weight of 500 or greater, more preferably 1000 or greater, and even more preferably 2000 or greater.

The antigen may be present either in or out of the cell. Preferably it is a molecule that is expressed on the surface of the cell membrane or that has an extracellular region since it facilitates detection by the antibody. As methods for contacting an intracellularly expressed antigen with the antibody, known methods may be used, including formaldehyde treatment. Most preferably, the antigen is a macromolecule having a region that is exposed extracellularly. Macromolecules include proteins, glycoproteins, proteoglycans etc., and the molecular weight is 10 kD or greater, preferably 50 kD or greater, and more preferably 100 kD or greater.

Macromolecules having an extracellular region include receptors of biologically active substances that are expressed on the surface of the cell membrane. For example, there can be mentioned the hematopoietic receptor family, the cytokine receptor family, the lymphokine receptor family, the TNF receptor family, the G protein-coupled receptor family, the tyrosine kinase receptor family, the serine/threonine receptor family, the tyrosine phosphatase receptor family, the adhesive factor receptor family, the hormone receptor family, and the like.

Cancer specific antigens or cancer-associated antigens are also included in the macromolecules having an extracellular region. Cancer specific antigens are molecules that impart to cancer substances properties different qualitatively and quantitatively from the original mother cell of the cancer. For example, they may be a sugar chain structure different from the normal, a conformation different from the normal, or an expression, in large quantities, different from the normal. More specifically, cancer specific antigens are antigens that are not expressed at all or expressed very little in the normal cells, and in the cancer cells the antigen cells etc. of which expression is increased are included in the cancer specific antigens. In many cases, they are enzymes, hormones, fetal proteins, gangliosides, which are proteoglycans, glycoproteins, glycolipids or proteins having no sugar chains.

According to the present invention, they are preferably antigens of which amount expressed is increased compared to that of the normal mother cell when the cells have become cancerous, or antigens that are not expressed in the normal cells but the expression of which is newly induced due to canceration. Cancer as used herein is cells that escape from the regulation in the normal growth and differentiation and thereby grow autonomously, and they may be malignant cancer or benign cancer.

The tissues or organs from which they are derived may be of any type, and may be cancer cells derived from blood cells, or cancer cells derived from various organs such as the liver, the kidney, the lung, the prostate, and the thyroid gland. Furthermore, they may be derived from epithelial cells, interstitial cells, or glandular cells. For example, the expression of HM1.24 antigen is known to be increased in myeloma cells, and hence is included in cancer specific antigens. There can also be used CEA antigen and ZCE-025 antibody in the colon cancer, CA125 and IMACIS-2 antibody in the ovarian cancer, p97 antigen and 96.5 antibody in the malignant melanoma, and the like.

The antibody for use in the present invention may be of any type, as long as it can bind to the desired antigen, and there can be used mouse antibody, rat antibody, rabbit antibody, goat antibody, chimeric antibody, humanized antibody, human antibody etc. as appropriate. The antibody may be polyclonal antibody or monoclonal antibody, and monoclonal antibody is preferred in that homogeneous antibody can be stably produced. Polyclonal antibody or monoclonal antibody can be prepared in methods known to those skilled in the art.

Hybridomas that produce monoclonal antibody can be basically constructed using a known procedure as described below. Thus, the desired antigen or the cells that express the desired antigen may be used as a sensitizing antigen and they are immunized in the conventional method of immunization. The immune cells thus obtained are fused with known parent cells in the conventional cell fusion process, and then screened by the conventional screening method to screen cells (hybridomas) that produce monoclonal antibodies. Hybridomas may be prepared by the method of Milstein et al. (Kohler, G. and Milstein, C., Methods Enzymol. (1981) 73: 3-46). When the immunogenicity of the antigen is low, it may be bound to a macromolecule such as albumin having immunogenicity, and then used for immunization.

A recombinant antibody which was produced by the recombinant gene technology in which an antibody gene was cloned from the hybridoma and integrated into a suitable vector which was then introduced into a host can be used (see, for example, Carl, A. K., Borrebaeck, and James, W. Larrick, THERAPEUTIC MONOCLONAL ANTIBODIES, published in the United Kingdom by MACMILLAN PUBLISHERS LTD. 1990). Specifically, from mRNA of the hybridoma, cDNA encoding the variable region (V region) of the antibody is synthesized using reverse transcriptase.

Once DNA encoding the V region of the desired antibody has been obtained, it may be ligated to DNA encoding the constant region (C region) of the desired antibody, which is then integrated into an expression vector. Alternatively, DNA encoding the V region of the antibody may be integrated into an expression vector which already contains DNA encoding the C region of the antibody. It is integrated into an expression vector so as to be expressed under the control of the expression regulatory region such as enhancer and promoter. Subsequently, the expression vector may be transformed into a host cell and the antibody can then be expressed therein.

In accordance with the present invention, artificially altered recombinant antibody such as chimeric antibody and humanized antibody can be used for the purpose of lowering heterologous antigenicity against humans. These altered antibodies can be produced using known methods. Chimeric antibody is antibody that comprises the variable region of heavy chain and light chain of non-human mammalian antibody such as mouse antibody and the constant region of heavy chain and light chain of human antibody, and can be obtained by ligating DNA encoding the variable region of mouse antibody and DNA encoding the constant region of human antibody, which is then integrated into an expression vector and introduced into a host for production of the antibody therein.

Humanized antibody which is also called reshaped human antibody has been made by transplanting the complementarity determining region (CDR) of non-human mammalian antibody such as mouse antibody into the CDR of human antibody. The general recombinant DNA technology for preparation of such antibodies is also known. Specifically, a DNA sequence which was designed to ligate the CDR of mouse antibody with the framework region (FR) of human antibody is synthesized by the PCR method from several divided oligonucleotides having sections overlapping with one another at the ends thereof.

The DNA thus obtained is ligated to DNA encoding the constant region of human antibody, and then is integrated into an expression vector, which is introduced into a host for antibody production (see European Patent Application EP 239400 and International Patent Application WO 96/02576). For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For chimeric antibody or humanized antibody, the C region of human antibody that exhibits cytotoxic activity is used. For example, as the C region of human antibody, human Cγ, for example Cγ1, Cγ2, Cγ3, and Cγ4 can be used. Among them, antibody having Cγ1 and Cγ3 in particular has potent cytotoxic activity, i.e. ADCC activity and CDC activity.

In addition, methods of obtaining human antibody are also known. For example, human lymphocytes can be sensitized in vitro with the desired antigen or cells expressing the desired antigen, and the resulting sensitized lymphocytes are fused with a human-derived myeloma cell, for example U266, and then the desired human antibody having the activity of binding to the desired antigen can be obtained (see Japanese Examined Patent Publication (Kokoku) No. 1-59878). Furthermore, a transgenic animal having a repertoire of human antibody genes can be immunized with antigen to obtain the desired antibody (see International Patent Application WO 93/12227, WO 92/03918, WO 94/02602, WO 94/25585, WO 96/34096, and WO 96/33735).

Furthermore, a method of obtaining human antibody by means of panning using a human antibody library is also known. For example, the variable region of human antibody is expressed on the surface of a phage by the phage display method as a single chain antibody (scFv) to select a phage that binds to the antigen. By analyzing the gene of the phage selected, the DNA sequence encoding the variable region of the human antibody that binds to the antigen can be determined. Once the DNA sequence of scFv that binds to the antigen is clarified, it is possible to construct an appropriate expression vector that contains said sequence and then to obtain human antibody. These methods are already known and can be found in WO 92/01047, WO 92/20791, WO 93/06213, WO 93/11236, WO 93/19172, WO 95/01438, and WO 95/15388.

When an antibody gene is isolated and then introduced into a suitable host to produce antibody, combinations of a suitable host and an expression vector can be used. When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5.

Known plant cells include, for example, those derived from the genus Nicotiana, more specifically cells derived from *Nicotiana tabacum*, which is subjected to callus culture. Known fungal cells include yeasts such as the genus Saccharomyces, more specifically Saccharomyces serevisiae, or filamentous fungi such as the genus Aspergillus, more specifically *Aspergillus niger*. When the prokaryotic cells are used, there are the production systems which employ bacterial cells. Known bacterial cells include *Escherichia coli* (*E. coli*), and *Bacillus subtilis*. By introducing via transformation the gene of the desired antibody into these cells and culturing the transformed cells in vitro, the antibody can be obtained.

For example, in order to obtain monoclonal antibody against HM1.24 antigen, the method of Goto, T. et al. (Goto, T. et al., Blood (1994) 84, 1922-1930) can be used. As HM1.24 antigen-expressing cells, human multiple myeloma cell lines, KPMM2 or KPC-32 (Goto, T. et al., Jpn. J. Clin. Hematol. (1991) 32, 1400), can be used for immunization. KPMM2 has been internationally deposited under the provisions of the Budapest Treaty on Feb. 22, 1994 with the Patent Microorganism Depository, the National Institute of Bioscience and Human Technology (Chuo Dai 6, 1-1, Higashi 1-chome, Tsukuba city, Ibaraki Pref., Japan) as FERM BP-7419.

Also, HM1.24 antigen may be immunized. HM1.24 antigen is a protein that is encoded by the nucleotide sequence set forth in SEQ ID NO: 1 and that has the amino acid sequence set forth in SEQ ID NO: 2. cDNA thereof has been inserted to the XbaI cleavage site of the pUC19 vector, and has been prepared as a plasmid pRS38-pUC19. *Escherichia coli* (*E. coli*) having the plasmid pRS38-pUC19 has been internationally deposited under the provisions of the Budapest Treaty as *Escherichia coli* DH5α (pRS38-pUC19) on Oct. 5, 1993 with the Patent Microorganism Depository, the National Institute of Bioscience and Human Technology (Chuo Dai 6, 1-1, Higashi 1-chome, Tsukuba city, Ibaraki Pref., Japan) as FERM BP-4434 (Japanese Unexamined Patent Publication (Kokai) No. 7-196694).

Furthermore, a hybridoma producing mouse monoclonal antibody (mouse anti-HM1.24 antibody) against HM1.24 antigen has been internationally deposited under the provisions of the Budapest Treaty on Apr. 27, 1995 with the Patent Microorganism Depository, the National Institute of Bioscience and Human Technology (Chuo Dai 6, 1-1, Higashi 1-chome, Tsukuba city, Ibaraki Pref., Japan) as FERM BP-5233.

A humanized antibody of monoclonal antibody against HM1.24 antigen deposited as FERM BP-5233 was constructed. Various versions of humanized anti-HM1.24 antibody were constructed by CDR substitution and the amino acid substitution of the FR region, and the activities thereof were confirmed. The version of humanized anti-HM1.24 antibody having the most preferred activity was the one in which the light chain is version a and the heavy chain is version s (see International Patent Publication WO 99/18212). The nucleotide sequence and the amino acid sequence of the light chain version a are set forth in SEQ ID NO: 3 and 4, respectively. The nucleotide sequence and the amino acid sequence of the heavy chain version s were set forth in SEQ ID NO: 5 and 6, respectively.

Incidentally, *E. coli* having the plasmid containing the light chain version a of humanized anti-HM1.24 antibody has been internationally deposited under the provisions of the Budapest Treaty as *Escherichia coli* DH5α (pUC19-RVLa-AHM-gk) on Aug. 29, 1996 with the Patent Microorganism Depository, the National Institute of Bioscience and Human Technology (Chuo Dai 6, 1-1, Higashi 1-chome, Tsukuba city, Ibaraki Pref., Japan) as FERM BP-5645. Also, *E. coli* having the plasmid containing the heavy chain version s of humanized anti-HM1.24 antibody has been internationally deposited under the provisions of the Budapest Treaty as *Escherichia coli* DH5a (pUC19-RVHs-AHM-gγ1) on Sep. 29, 1997 with the Patent Microorganism Depository, the National Institute of Bioscience and Human Technology (Chuo Dai 6, 1-1,1 Higashi 1-chome, Tsukuba city, Ibaraki Pref., Japan) as FERM BP-6127. In the present specification, the humanized anti-HM1.24 antibody having the light chain version a and the heavy chain version s is specifically referred to as AHM.

Fluorescence-labelled antibodies can be prepared as appropriate using commercially available reagents. For example, FITC, Fluorescein, AMCA, TRITC, Texas Red (all of them are available from Pierce Chemical Company) etc. can be used. Flow cytometric analysis is a well-known method and will not be specifically explained herein. For example, the following procedure can be used. After washing the test cells with PBS(-), a fluorescence-labelled antibody or a control antibody diluted to predetermined concentrations in FACS/PBS (PBS(-) containing 0.1% fetal bovine serum and 0.1% sodium azide) is added thereto, and incubated on ice for 30 minutes. After washing in FACS/PBS, it is suspended in 0.5 ml to 1 ml of FACS/PBS, and the fluorescence intensity of the cells is determined using FACScan (manufactured by Becton Dickinson) or EPICS XL (manufactured by Beckman Coulter).

One aspect of the present invention relates to a method of formulating an equation of correlation between the amount expressed of antigen and fluorescence intensity. Thus, it relates to a method of obtaining an equation of correlation for calculating the amount expressed of antigen to which said antibody binds. The antibody that specifically binds to the desired antigen may be a commercially available antibody or may be prepared in the above-mentioned method. Furthermore, it may be a commercially available fluorescence-labelled antibody or an antibody labelled with fluorescence using reagents for fluorescence labelling. Furthermore, an antibody (primary antibody) that binds to the desired antigen may be labelled with fluorescence, or an secondary antibody that binds to primary antibody may be labelled with fluorescence.

When a primary antibody labelled with fluorescence is used, the test cells are reacted with the primary antibody and then fluorescence intensity may be determined. When a secondary antibody labelled with fluorescence is used, a primary antibody not labelled with fluorescence and the test cells are reacted, and then the secondary antibody labelled with fluorescence is reacted, and then fluorescence intensity is determined. Preferably a primary antibody labelled with fluorescence is used, because the error of measurement is smaller. When an antigen of which amount expressed is small is determined, a fluorescence-labelled polyclonal antibody may be used as a secondary antibody.

The titer of a fluorescence-labelled antibody may be maintained at a constant level using a standard reagent. The titer of a fluorescence-labelled antibody depends on the binding activity (affinity for antigen) of the antibody and the binding efficiency of the fluorescence to the antibody. For example, even if the binding activity is equal, the titer of the antibody may be different when the binding efficiency of the fluorescence is different, and even if the binding efficiency of the fluorescence is identical, the titer of the fluorescence-labelled antibody may be different when the binding activity is different.

According to the present invention, the fluorescence-labelled antibody can be used as long as the titer of the fluorescence-labelled antibody used to formulate the equation of correlation and titer of the fluorescence-labelled antibody used to determine the amount expressed of antigen are the same. Preferably, the fluorescence-labelled antibody used to formulate the equation of correlation and the fluorescence-labelled antibody used to determine the amount expressed of antigen are the same fluorescence-labelled antibody. In general, fluorescence-labelled antibodies having the same titer can be prepared as long as purified antibody is used and labelled with a fluorescence label according to the instructions provided by the supplier.

In order to confirm that the titer of a newly prepared fluorescence-labelled antibody is equal to that of the previously used fluorescence-labelled antibody, antigen-bound beads (antigen beads) are used and the fluorescence intensity of the antigen beads by each fluorescence-labelled antibody is determined and compared. Also, cells that have been shown to express the antigen may be used in stead of the antigen beads. As long as the measurement of the new and old fluorescence-labelled antibodies is performed in parallel, changes with time in the amount of antigen bound to the beads or the amount of antigen expressed in the cells may be neglected.

Antigen beads may be prepared using commercially available beads. For example, there can be used commercially available EZ-Link (trade mark) Sulfo-NHS-LC-Biotin (PIERCE) or Streptavidin Coated Carboxylated Microspheres (Polysciences). Antigen used for the preparation of antigen beads may be full-length or partial fragments, and as long as the binding activity to antibody is retained, the length of the amino acid sequence is not limited. As partial fragments of antigen, secretory form antigen having an extracellular region and having no intracellular region or transmembrane region may preferably used.

Once a set of antigen beads and fluorescence-labelled antibody are prepared, either of them may be used as a standard to confirm the titer of newly prepared antigen beads or fluorescence-labelled antibody and to prepare it. The titer of antigen beads depends on the number of antigens bound to a bead. When the number of antigens per bead is equal, the titer of antigen beads is equal. Usually, when the amino acid sequence of the antigen used, the concentration of the antigen used in the binding reaction with beads, the composition of the reaction solution, and temperature are equal, antigen beads of the same titer can be prepared.

A plurality of cell groups for which the amount expressed of the desired antigen has previously been determined may be cell groups having different genetic backgrounds or cell groups having the same genetic backgrounds. For example, as long as there are no other antigens present than the desired antigen to which the fluorescence-labelled antibody binds, they may be of different genetic background. Also, the cells constituting the cell group may be or may not be cell lines. For example, they may be cells isolated from a living body or primary cultured cells. As cell groups of different genetic background, there can be used cell line A, cell line B, and cell line C for which the amounts expressed of the desired antigen are different. Furthermore, it is also possible that cell line A is divided depending on the amount expressed of the antigen and used as cell line A—high expression, cell line A—moderate expression, and cell line A—low expression. These cells are cell groups having the same genetic background.

Preferably, a plurality of cell groups are prepared for which the genetic background is the same and the amount expressed of said antigen is only different. For example, a gene encoding the antigen is introduced into an suitable vector. Then, a host cell not expressing said antigen is selected, into which the above expression vector is introduced. The transformed cells thus prepared are reacted to the fluorescence-labelled antibody, and aliquoted into a plurality of cell groups having different fluorescence intensity using a flow cytometer. For example, they can be divided into a cell group exhibiting strong fluorescence intensity, a cell group exhibiting moderate fluorescence intensity, and a cell group exhibiting weak fluorescence intensity.

Aliquoted cells may be rendered a single cell line by limited dilution etc., and may be cultured to expand to prepare a homogeneous cell group. The fluorescence intensity of the culture-expanded transformed cells is determined, and a plurality of cell groups having different amounts expressed of said antigen are selected as appropriate. The plurality of cell groups thus selected may be used as standard cells for formulating an equation of correlation as the plurality of cell groups having different amounts expressed of antigen. Standard cells as used herein means a cell group for which the amount expressed of antigen has previously been determined and which is used for correlation analysis at the time of formulating an equation of correlation between the amount expressed of antigen and fluorescence intensity.

The larger the number of cells for the plurality of cell groups to be used as the standard cells, the more precisely an equation of correlation can be formulated. Usually two to ten cell groups may be used, and preferably two cell groups, more preferably three cell groups, even more preferably four cell groups, and most preferably five cell group may be used as the standard cells. The amounts of antigen expressed in the standard cells for use in formulating an equation of correlation are preferably different to the extent that the difference can be detected. In the plurality of standard cell groups, the amounts expressed of antigen in the cell group that exhibits the minimum amount expressed and the cell group that exhibits the maximum amount expressed are preferably different by at least five times or more, more preferably ten times or more, even more preferably 100 times or more, and most preferably 1000 times or more.

In order to quantitate in advance the amount expressed of antigen in a plurality of cell groups having different amounts expressed of antigen, the Scatchard method using antibody labelled with a radioisotope can be used. As the radioisotope, iodine 125 is most commonly used. This method is known to those skilled in the art, and is described for example in "Shinseikagaku Jikken Kouza 12, Bunshi Mennekigaku I (New Biochemistry Experiment Series 12, Molecular Immunology I), Tokyo Kagaku Dojin Co., Ltd." pp. 170-176.

Methods of analyzing a correlation between the amount expressed of antigen that has previously been quantitated and fluorescence intensity are not specifically limited, and the fluorescence intensity is converted to the Log MEFL value, for which correlation with the amount expressed of antigen is analyzed. MEFL (molecules of equivalent fluorescein) is a unit for fluorescence intensity used in SPHERO (trade mark) Rainbow Calibration Particles (8 peaks) (SPHERO-beads) for use in the calibration of flow cytometry, and for eight beads, the MEFL value of 330000, 140000, 40000, 15000, 4700, 1800, 600, and 100 have been alloted, respectively. Thus, by plotting said eight MEFL values and a mean of fluorescence intensity patterns measured from flow cytometry, a standard curve may be constructed, and using said standard curve, a MEFL value can be calculated from the fluorescence intensity pattern of an unknown sample.

As the mean value obtained from a fluorescence intensity pattern, there are two ways of determining the value: the Mean and the Geo Mean. In the Mean, fluorescence intensity is calculated in terms of Log scales, whereas the Geo Mean uses the resolution of scales. Therefore, more precise mean values of fluorescence intensity can be obtained by the Mean, whereas values close to the average position of the cell population can be obtained as the Geo Mean. Both values are not greatly different from each other, but the Geo Mean is preferably used in the method of the present invention. The Geo Mean and the Mean can be easily calculated using a flow cytometry analysis software.

For example, in order to obtain a standard curve of fluorescence intensity and the MEFL values of cells using SPHERO-beads, one drop of SPHERO-beads is added to one ml of FACS/PBS, and a fluorescence intensity histogram is determined. Logarithm of the Geo Mean of each peak (Log Geo Mean) is calculated. On the other hand, logarithm of MEFL values given to respective beads (Log MEFL values) is calculated, and then the Log MEFL values are plotted against the Log Geo Mean values to make a standard curve. If the Log Geo Mean value is set as X and the Log MEFL values is set as y, the relationship is generally expressed by y=Ax+B (A and B are constants). Thus, by substituting the Log Geo Mean values obtained by the flow cytometry of test cells for x, the Log MEFL values of the test cells can be obtained.

In order to obtain a equation of correlation between the Log MEFL value and the amount of antigen, the Geo Mean of fluorescence intensity is determined for a plurality of cell groups for which the amount expressed of antigen has previously been quantitated, and the Log Geo Mean value is calculated. Then, the Log MEFL value is determined from the standard curve to obtain a equation of correlation with the amount expressed of antigen. Specifically, with a plurality of cell groups for which the amount expressed of antigen has previously been quantitated as the test cells, the Geo Mean of fluorescence intensity is obtained by flow cytometry. At this time, after determination using a fluorescence-labelled antibody that specifically reacts to the antigen, a control antibody labelled with fluorescence is used to determine a value, and the difference between the two Geo Means is set as a Geo Mean specific to the antigen.

The Log Geo Mean value is calculated, and the Log MEFL value is determined from the standard curve. Then, the Log MEFL value is plotted on the X-axis and the amount expressed of antigen determined using a radioisotope etc. is plotted on the Y-axis. In general, as an equation of correlation, it can be formulated as $$Y=Ae^{Bx}$$

wherein A and B are constants determined by the combination of antigen and antibody. Thus, once the Log MEFL value of an unknown sample is obtained, the amount expressed of antigen can be quantitated using a equation of correlation $$Y=Ae^{Bx}$$

Coefficient of correlation is preferably 0.8 or greater, more preferably 0.9 or greater, even more preferably 0.95 or greater, and most preferably 0.98 or greater.

Once a fluorescence-labelled antibody has been prepared and the above equation of correlation between the amount expressed of antigen and fluorescence intensity has been revealed using said fluorescence-labelled antibody, it is possible to determine fluorescence intensity by flow cytometry using a fluorescence-labelled antibody for any cell, and to calculate, from the Log MEFL values obtained, the amount of antigen expressed in the cell.

As the test cells, any cell can be used. For example, they may be cell lines or cells collected from normal healthy subjects and patients. Cells collected from normal healthy subjects and patients may be cultured or may not be cultured prior to being used. Alternatively, cells that were frozen may be thawed and used. Cells to be used as test cells are not specifically limited, as long as they have been isolated so as to be measured by flow cytometry.

For example, cells and tissues are collected from normal healthy subjects and patients, and the desired cells are isolated to prepare test cells. As methods of isolating and preparing the desired cells from tissues and cell populations, known methods can be used. For example, tissues are harvested from an organ such as the liver and the kidney, and the tissue obtained is subjected to enzyme treatment to isolate single cells, as appropriate, to prepare test cells. In the case of blood cell populations harvested from the peripheral blood or the bone marrow, blood cells are isolated, as appropriate, by the density gradient separation method etc. to isolate the desired cells as test cells prior to use.

The kit for use in the measurement of the amount expressed of antigen only needs to include at least a fluorescence-labelled antibody and an instruction manual for calculating the amount of antigen from fluorescence intensity. Preferably, the instruction manual for calculating the amount of antigen describes an equation of correlation between the amount expressed of antigen and fluorescence intensity. The fluorescence-labelled antibody may be supplied in a liquid form or a lyophilized form.

When it is supplied in a liquid form, the concentration of antigen is not specifically limited. From the viewpoint of stability, however, it is preferably 0.01 mg/ml to 100 mg/ml, more preferably 0.1 mg/ml to 10 mg/ml, even more preferably 0.5 mg/ml to 5 mg/ml, and most preferably 1 mg/ml to 3 mg/ml. In the case of a lyophilized product, it is dissolved immediately prior to use. Thus, the kit preferably includes an instruction manual that describes the method of dissolution, preferably the composition of the solution, and the quantity. More preferably, the kit contains a lyophilized fluorescence-labelled antibody and a dissolution solution. Furthermore, a reaction solution for use in contacting the fluorescence-labelled antibody with test cells may be contained in the kit.

Another aspect of the present invention relates to a method of creating an equation of correlation with the drug therapy or diet therapy of patients with the antigen as the target for measurement, the expression of said antigen being induced or being increased in specific diseases, to a method of estimating patient's sensitivity to drug therapy or diet therapy, to a method of identifying the condition of patients, or to a method of diagnosing patients.

In a method of formulating the correlation of sensitivity of patients to a drug therapy or a diet therapy, any antigen may be selected. For example, a plurality of antigens suspected of affecting the sensitivity of patients may be selected to determine antigens having correlation with sensitivity to a drug therapy or antigens for which the presence of correlation is expected may be selected, and then correlation of said antigens to the sensitivity of patients is confirmed.

In a method of formulating the correlation of sensitivity of patients to a drug therapy or a diet therapy, a group (patient group) of patients comprising a plurality of patients may be selected. The patient group is a population comprising a plurality of patients classified into a particular disease. It is a population comprising preferably at least five, more preferably at least 10, even more preferably at least 30, and most preferably at least 50 subjects. Using a fluorescence-labelled antibody, the amount of antigen expressed in the cells collected from individual patients included in the patient group is determined.

Subsequently, the same patients are subjected to a drug therapy, and the therapeutic effect of said drug therapy in said patients is assessed in a quantitative or qualitative manner. The qualitative assessment may be a classification of the effect of the drug therapy. For example, it may be classified into three classes: the patient group for which remarkable effect was observed, the patient group for which effect was observed, and the patient group for which no effect was observed. The patient group to be classified is at least two stages (with or without effect), preferably at least three stages, more preferably at least four stages, and most preferably at least five stages of assessment.

Then, the amount expressed of antigen in the patients belonging to each class and the therapeutic effect of said drug therapy are compared to analyze correlation. In the correlation analysis, means of amounts expressed of antigen of the patients belonging to each class may be used, or analysis of variance maybe used. The result obtained by correlation analysis may be formulated as correlation. The correlation of a drug therapy and the sensitivity of patients to the drug therapy is expressed as a numerical value having a certain range. For example, there may be illustrated "80% of the patients with the amount expressed of antigen being 10000 or greater exhibit a highly favorable response to said drug therapy", or "for the patients with the amount expressed of antigen being 1000 to 10000, moderate therapeutic effect may be expected."

Once the correlation between the amount of antigen expressed in the cells derived from the patients and the sensitivity of patients to any drug therapy has been clarified, it becomes possible to predict the sensitivity of a patient to the drug therapy. Specifically, cells are collected from the subject patients, said cells are reacted to a fluorescence-labelled antibody, and fluorescence intensity is measured by flow cytometry. From the fluorescence intensity obtained, Log Geo Mean values are calculated and log MEFL values are determined to calculate the amount expressed of antigen. By fitting the amount expressed of antigen obtained to the correlation of sensitivity of the subject patients to said drug therapy, the sensitivity of the subject patients to said drug therapy can be predicted. Thus, it is possible to predict the extent of effect to which said drug therapy is effective to said patients.

The regimen of treatment included in the drug therapy is not specifically limited as long as it is a method of treatment using drugs, but it is preferably an antibody therapy that utilizes antibody as the drug. In formulating equation of correlation for predicting the sensitivity of patients to the antibody therapy, it is preferable to formulate equation of correlation between an amount of antigen to which an antibody used for the antibody therapy binds and an effect of the therapy. Antibody for use in the antibody therapy may be whole antibody or antibody fragments. As long as the binding activity with antigen is retained, any antibody fragments may be used, and preferably they are fragments comprising an antigen binding site.

Fragments comprising an antigen binding site may be Fab, F(ab)'2, Fv, single stranded Fv, and a diabody composed of two molecules of single stranded Fv2. In antibodies and antibody fragments for use in antibody therapy, the antibody per se need not be a drug, and may be used for transporting the drug having a therapeutic effect to an appropriate site. For example, a missile therapy composed of a combination of an anti-cancer agent and an antibody is encompassed in the antibody therapy of the present invention. In the missile therapy, the antibody may be covalently bound to any anti-cancer agent to form a complex, or may be bound to a radioisotope having a cytocidal effect.

Also, microcapsules or nanocapsules containing an anti-cancer agent or a radioisotope may be prepared, and antibody may be bound to the surface of said capsules. The antibody for use in the missile therapy may be antibody that specifically binds to an antigen expressed specifically in the target cell, and is expected to exhibit a favorable correlation between the amount expressed of antigen and the therapeutic effect of the antibody therapy, i.e. the sensitivity of patients to said antibody therapy. Thus, if the amount expressed of said antigen can be determined in a quantitative manner, and its correlation with the sensitivity of patients is clarified, it would become possible to predict the effect of the antibody therapy prior to the treatment.

The antibody therapy includes a method of treatment comprising administering an antibody that has cytotoxicity per se. Cytotoxicity includes ADCC activity, CDC activity, apoptosis-inducing activity etc. The antibody therapy that uses an antibody having cytotoxicity is mainly used for the treatment of cancer. For example, there can be mentioned a method of treating cancer using anti-Her2 antibody. Furthermore, an antibody therapy that employs an antibody having a neutralizing activity for therapeutic purposes is also encompassed in the present invention. For example, antibodies having an activity of neutralizing biologically active substances may be used for the treatment of diseases derived from said biologically active substances.

Antibody having a neutralizing activity is expected to exhibit a therapeutic effect by inhibiting the incorporation of biologically active substances into cells or the binding of the biologically active substances to receptors on the cell. Biologically active substances include secretory proteins such as cytokines, lymphokines, hormones, and there can be mentioned, for example, a rheumatoid therapy using a neutralizing antibody to TNF-α receptor. In these antibody therapies, Her2 and TNF-α receptors are antigens expressed on the surface of the cells, and if the amount expressed of Her2 and TNF-α antigens expressed on the surface of cells in patients could be determined, the sensitivity of patients to the antibody therapy can be predicted.

Fluorescence-labelled antibodies for use in a method of formulating the correlation of sensitivity of patients to a antibody therapy and fluorescence-labelled antibodies for use in a method of predicting the sensitivity of patients are preferably the same antibodies as are used in the antibody therapy, or may be different antibodies, as long as the titer or the antigen-binding activity of the antibodies is equal. For example, mouse antibody may be used as a fluorescence-labelled antibody to formulate correlation, and the amount of antigen expressed in the test cells derived from patients is determined. On the other hand, in the antibody therapy, a chimeric antibody or humanized antibody of said mouse antibody can be used. In general, it is known that chimeric antibody has the same antigen-binding activity, and humanized antibody has an almost equal antigen-binding activity, to the mouse antibody.

The ADCC activity of antibody can be generally determined as follows. First, mononuclear cells are isolated from human peripheral blood by density gradient method to prepare effector cells (E). On the other hand, target cells (T) are labelled with 51Cr. Then, the antibody to be measured for ADCC activity is added to target cells and incubated, and then effector cells at an appropriate ratio to the target cells are added and incubated.

After incubation, the supernatant is removed, and the radioactivity thereof is determined by a gamma counter. At this time, 1% NP-40 can be used for the measurement of maximum released radioactivity. Cytotoxicity (%) can be calculated by (A-C)/(B-C)×100. A is a radioactivity (cpm) released in the presence of antibody, B is a radioactivity (cpm) released by NP-40, and C is a radioactivity (cpm) released by only the culture liquid without antibody.

Furthermore, more potent ADCC activity or CDC activity may be induced by the addition, alteration, or modification of amino acids of the C region of antibody. There can be mentioned, for example, the conversion of IgG to IgM polymer by amino acid substitution (Smith, R. I. F. & Morrison, S. L. BIO/TECHNOLOGY (1994) 12, 683-688), the conversion of IgG to IgM polymer by amino acid addition (Smith, R. I. F. et al., J. Immunology (1995) 154, 2226-2236), the expression of a gene encoding L chain by direct ligation (Shuford, W. et al., Science (1991) 252, 724-727), the dimerization of IgG by amino acid substitution (Caron, P. C. et al., J. Exp. Med. (1992) 176, 1191-1195, Shopes, B., J. Immunology (1992) 148, 2918-2922), the dimerization of IgG by chemical modification (Wolff, E. A. et al., Cancer Res. (1993) 53, 2560-2565), and the introduction of effector function by the amino acid alteration of the antibody hinge region (Nordenhaug, L. et al., Eur. J. Immunol. (1991) 21, 2379-2384). These can be attained by oligomer site-directed mutagenesis using primers, the addition of a nucleotide sequence using restriction enzyme cleavage sites, and the use of a chemical modifying agent causing covalent bonding.

Apoptosis-inducing activity is an activity that induces programmed cell death, and can be detected by the binding of annexin V, fragmentation of DNA, cell shrinkage, and an apoptotic body.

The method of the present invention may be preferably used in an antibody therapy using an antibody (anti-HM1.24 antibody) against HM1.24 antigen. As anti-HM1.24 antibody, humanized anti-HM1.24 antibody is preferred. HM1.24 antigen is an antigen that is abundantly expressed on myeloma cells, and the treatment of myeloma through ADCC activity possessed by anti-HM1.24 antibody is promising. Thus, one preferred aspect of the present invention is an antibody therapy using humanized anti-HM1.24 antibody having Cγ1 as the human constant region, wherein the amount expressed of HM1.24 antigen expressed on the myeloma cells of patients is quantitated in order to predict the sensitivity of patients to the antibody therapy using humanized anti-HM1.24 antibody.

As the antibody for use in quantitating the amount of HM1.24 antigen expressed on the myeloma cells of patients and in formulating the equation of correlation of the amount expressed of HM1.24 antigen and fluorescence intensity, there can be used humanized anti-HM1.24 antibody for use in the antibody therapy or mouse anti-HM1.24 antibody which humanized antibody was based on, and more preferably humanized anti-HM1.24 antibody is used.

An equation of correlation between fluorescence intensity (log MEFL) obtained using humanized anti-HM1.24 antibody and the number of antigens may be expressed by $$Y=2.53e^{2.15 \log MEFL}$$

Using said equation of correlation, the amount expressed of HM1.24 antigen can be calculated from the fluorescence intensity of test cells by fluorescence-labelled humanized anti-HM1.24 antibody. Also, from the kit containing the instruction manual describing said equation of correlation and a fluorescence-labelled humanized anti-HM1.24 antibody, sensitivity against the antibody therapy with humanized anti-HM1.24 antibody can be predicted. Furthermore, as the expression of HM1.24 antigen is increased in the myeloma cells compared to the normal cells, it can also be used for the diagnosis of myeloma.

Since humanized anti-HM1.24 antibody is likely to have an effect on hematopoietic tumors in general, and specifically it has an effect on lymphatic tumors, plasmacytoma, and myeloma, in particular multiple myeloma, it can be used to predict the sensitivity of these patients to antibody therapy using humanized anti-HM1.24 antibody, to diagnose diseases, or to estimate the degree of progression of diseases. As lymphatic tumors, there can be mentioned acute B-lymphocytic leukemia (B-ALL), chronic B-lymphocytic leukemia (B-CLL), pre-B lymphoma, Burkitt lymphoma, follicular lymphoma, mantle cell lymphoma, diffuse lymphoma, acute T-lymphocytic leukemia (T-ALL), chronic T-lymphocytic leukemia (T-CLL), adult T cell leukemia (ATL), non-ATL peripheral T-lymphoma (PNTL) and the like.

For anti-tumor effect of humanized anti-HM1.24 antibody, if the expression of 2000 or more antigens are confirmed per test cell, the antibody therapy with humanized anti-HM1.24 antibody is predicted to have an effect, and more preferably when 1000 or more antigens are expressed per cell, even more preferably 5000 or more antigens, and most preferably 10000 or more antigens are expressed per cell, the antibody therapy with humanized anti-HM1.24 antibody is predicted to be effective.

When it is used for the diagnosis of patients, it is necessary that the association of amount expressed of antigen with the disease has been elucidated. The association of amount expressed of antigen with the disease means that it is not expressed in the normal healthy subjects but is expressed when afflicted with a disease, or that the amount expressed is increased in patients afflicted with a disease compared to the amount expressed of antigen in the normal healthy subjects. The enhanced expression is preferably 10-fold or greater, more preferably 100-fold or greater, and most preferably 1000-fold or greater.

In accordance with the present invention, it is possible to elucidate the association of the amount expressed of antigen with a disease. After the steps of selecting a group of patients, selecting a group of normal healthy subjects and selecting a plurality of appropriate antigens, test cells are collected from patients and normal healthy subjects, the amount expressed of antigen is determined for both of the patient and the normal healthy subject groups, and an antigen may be selected that has correlation with the degree of the amount expressed of antigen in the patients and the normal healthy subjects. The amount expressed of antigen may be high in the normal healthy subjects and low in the patients, or low in the normal healthy subjects and high in the patients. Preferably there is a difference in the amount expressed of antigen between the patient group and the normal healthy subject group. The measurement of significant difference may be calculated by a common statistical analysis, and preferably by Student's t-test, and the p value is 0.2 or less, more preferably 0.1 or less, and most preferably 0.05 or less.

If the amount expressed of antigen and the degree of progression of disease have been revealed, cells collected from patients are used as test cells, and the amount of antigen expressed in said test cells is determined by using Fluorescence-labelled antibody, and then the degree of progression of disease can be estimated from the amount expressed of said antigen. For example, antigens (cancer antigen) specifically expressed in cancer cells are used as the target molecules, and by determining the amount expressed of said cancer antigen using a fluorescence-labelled antibody against said antigen, the degree of cancer progression can be estimated.

Pharmaceutical compositions comprising the antibody of the present invention as an active ingredient can be parenterally administered either systemically or locally. For example, intravenous injection such as drip infusion, intramuscular injection, intraperitoneal injection, subcutaneous injection may be selected, and the method of administration may be selected as appropriate depending on the age and condition of patients. Effective doses for antibody are selected from the range of 0.01 mg/kg to 100 mg/kg body weight per administration. Alternatively, doses of 1-1000 mg, preferably 5-300 mg, and more preferably 10-100 mg per patient may be selected. Depending on the route of administration, pharmaceutically acceptable carriers or additives may be included.

Examples of such carriers and additives include water, pharmaceutically acceptable organic solvents, collagen, polyvinyl alcohol, polyvinyl pyrrolidone, carboxyvinyl polymer, carboxymethyl cellulose sodium, sodium polyacrylate, sodium alginate, water soluble dextran, carboxymethyl starch sodium, pectin, methyl cellulose, ethyl cellulose, xanthane gum, gum Arabic, casein, gelatin, agar, diglycerin, propylene glycol, polyethylene glycol, vaseline, paraffin, stearyl alcohol, stearic acid, human serum albumin (HSA), mannitol, sorbitol, lactose, pharmaceutically acceptable surfactants and the like. Additives used may be selected from, but are not limited to, the above or are used in combination therewith.

EXAMPLES

The present invention will now be explained in further details with reference to the following Examples.

Example 1

Flow Cytometric Analysis of the Amount of HM1.24 Antigen (1) Materials for the Experiment As human hematopoietic tumor cell lines, KPMM2 (International Deposit Number FERM BP-7419), RPMI8226 (ATCC CCL-155), U266B1 (ATCC TIB-196) (these are multiple myeloma), ARH-77 (ATCC CRL-1621) (plasma cell leukemia), IM-9 (ATCC CCL-159) (B lymphoblast), and HS-Sultan (ATCC CRL-1484) (plasmacytoma) were used.

For subculturing of these cell lines, an RPMI1640 medium (Cat. No. 31800, GIBCO BRL) (hereinafter referred to as 10% FBS/RPMI medium) supplemented with 10% fetal bovine serum (FBS, Cat. No. SH30071.03, Lot No. AHK9081, HyClone laboratories), 55 μmol/l 2-mercaptoethanol (Cat. No. 21985-023, GIBCO BRL), and 0.1 mg potency/ml kanamycin sulfate (kanamycin sulfate for injection Meiji, Meiji Seika Kaisha Ltd.) was used. For subculturing of KPMM2 cells, RPMI1640 medium containing 20% FBS was used, and recombinant human IL-6 was added to a final concentration of 4 ng/ml.

Peripheral blood mononuclear cells (PBMC) derived from normal healthy subjects were prepared immediately prior to use. Thus, using a syringe in which about 5 ml of 1000 units/ml of heparin solution (Novo Heparin for injection 1000, Hoechst Marion Roussel) has previously been injected, about 50 ml of peripheral blood was collected from normal healthy volunteers. The peripheral blood was diluted two-fold in Dulbecco's phosphate buffered saline (-) (PBS(-), Code No. 05913, Nissui Pharmaceutical Co., Ltd.), and aliquoted into 12 tubes.

In order not to be mixed with peripheral blood, about 2.5 ml of Ficoll-Paque (trade mark) PLUS (Code No. 17-1440-02, Amersham Pharmacia Biotech AB) was dispensed in each tube. This was centrifuged (500×g, 30 minutes, 20° C.), and then the interphase which is the fraction of mononuclear cells was collected, and washed twice in MEM medium (Cat. No. M2645, SIGMA) supplemented with 5% FBS, and 0.1 mg potency/ml kanamycin sulfate. The cell pellets obtained were suspended in the same medium to prepare PBMC.

Human bone marrow-derived mononuclear cells (BM-MNC) derived from patients with myeloma were prepared in the following manner. Thus, 3 ml of heparin-treated bone marrow puncture samples were collected from patients with myeloma, to which 7 ml of serum-free Hanks' balanced salt solution (HBSS) was added for dilution. Three ml of Ficoll-Paque (trade mark) PLUS was layered thereonto, and centrifuged (1500 rpm, 30 minutes, 20° C.). The interphase which is the fraction of mononuclear cells was collected, and after suspending in 7 ml of serum-free HBSS, it was centrifuged (1500 rpm, 5 minutes, 20° C). The cell pellets obtained were suspended in RPMI1640 medium supplemented with 10% FBS to prepare BMMNC.

As an alternative method, the following method was used. Thus, to 10 ml of heparin-treated bone marrow puncture samples, 10 ml of serum-free HBSS and 200 [l of Red-Out (Cat. No. 1069-00-0, Robbins Scientific) was added, and then they were allowed to stand at room temperature for 5 minutes. This was layered on the Ficoll-Paque (trade mark) Research grade (Cat. No. 17-0840-02, Amersham Pharmacia Biotech AB), and was centrifuged (1600-1800 rpm, 20 minutes). The interphase was collected, and after suspending in HBSS supplemented with 5% FBS, it was centrifuged (1500 rpm, 5 minutes). The cell pellets obtained were suspended in IMDM medium supplemented with 20% FBS to prepare BMMNC.

The light chain of the humanized anti-HM1.24 antibody used in this example is version a, the heavy chain is version s (see International Patent Publication WO99/18212), and the nucleotide sequence and the amino acid sequence of the light chain version a have been set forth in SEQ ID NO: 3 and 4, respectively (FERM BP-5645). The nucleotide sequence and the amino acid sequence of the heavy chain version s have been set forth in SEQ ID NO: 5 and 6, respectively (FERM BP-6127). As used herein, the humanized anti-HM1.24 antibody having said amino acid sequence is referred to as AHM.

The control antibody human IgG1 (hIgG1) antibody is Human IgG1, Kappa (Cat. No. 13889, Lot No. 109H9179, Supplier: SIGMA). According to the instructions from the supplier, it was dissolved in PBS(-) to a concentration of 1.0 mg/ml to prepare a hIgG1 solution. This was aliquoted and stored at −25° C., and thawed immediately prior to use. This control antibody is a human antibody of which the isotype is identical to humanized anti-HM1.24 antibody, and which does not contain preservatives.

Soluble human HM1.24 antigen was prepared by the method of Biochemical and Biophysical Research Communications 258, 583-591 (1999). The amino acid sequence has the amino acid sequence from Asn at position 49 to Gln at position 180 in the amino acid sequence set forth in SEQ ID NO: 2.

The bicarbonate buffer was prepared by dissolving each of 0.210 g of $NaHCO_3$ (Special grade, Code No. 312-13, Nacalai Tesque Inc.) and 0.265 g of $Na_2CO_3$ (Special grade, Code No. 313-11, Nacalai Tesque Inc.) in 50 ml Milli Q water, and mixing 50 ml of an aqueous solution of $NaHCO_3$ and 1 ml of an aqueous solution of $Na_2CO_3$ to prepare 50 mmol/l of bicarbonate buffer. pH was 8.61. All the solutions prepared were stored at 5° C.

The NHS-fluorescein solution was prepared by dissolving NHS-fluorescein (Cat. No. 46100, PIERCE) in DMSO (Special grade, Cat. No. 35535-0330, Junsei Kagaku Co., Ltd.) to a concentration of 1 mg/ml.

FACS/PBS was prepared by dissolving 1 g of bovine serum albumin (BSA, RIA grade, Cat. No. A7888, SIGMA) in 1 l of CellWASH (PBS(-) containing 0.1% $NaN_3$, Cat. No. 349524, Becton Dickinson). It was stored at 5° C.

The Blocking Buffer was prepared by dissolving human IgG (Code No. 55908, ICN) in FACS/PBS to a concentration of 5 mg/ml. It was stored at 5° C.

The fluorescence-labelled beads were SPHERO (trade mark) Rainbow Calibration Particles (8 peaks), 3.0-3.4 μm (Cat. No. RCP-30-5A, Spherotech) (SPHERO-beads) which were used as they were. SPHERO (trade mark) Rainbow Calibration Particles are a mixture of beads exhibiting 8 different fluorescence intensities, and used for calibration of flow cytometers. The fluorescence intensity of each bead is defined by the MEFL (molecules of equivalent fluorescein) units, and the values are 330,000, 140,000, 40,000, 15,000, 4,700, 1,800, 600, and 100.

Humanized anti-HM1.24 antibody-fluorescein was prepared by a conventional method. Thus, 555.6 μl of humanized anti-HM1.24 antibody stock solution (18.0 mg/ml) was diluted in 1444.4 μl of the bicarbonate buffer to prepare a humanized anti-HM1.24 antibody at a concentration of 5 mg/ml. Two hundred μl of NHS-fluorescein was added thereto, and reacted on ice for 2 hours to label humanized anti-HM1.24 antibody with fluorescein.

Then, using a PD-10 column (Cat. No. 17-0851-01, Amersham Pharmacia Biotech AB) equilibrated with PBS(-), desalting by gel filtration was performed. After determining the protein concentration by the Bio-Rad Protein Assay Dye Reagent Concentrate (Cat. No. 500-0006, BIO-RAD), it was diluted in FACS/PBS to 1 mg/ml, and stored at a set temperature of 5° C. A portion of this solution was diluted to 200 μg/ml in FACS/PBS to prepare humanized anti-HM1.24 antibody-fluorescein, and 1 ml aliquots thereof were stored at a set temperature of −80° C. Prior to use it was thawed and stored at a set temperature of 5° C.

A fluorescence-labelled control antibody (hIgG1-fluorescein) was prepared in the following manner. Thus, after 4 mg of human IgG1 (hIgG1, Human IgG1, Kappa, Cat. No. I3889, SIGMA) was dissolved in 4 ml of PBS(-), it was filtered by MILLEX-GV 0.22 μm Filter Unit (Cat. No. SLGV025LS, MILLIPORE). To this was added 400 μl of NHS-fluorescein solution, which was then reacted on ice for 2 hours to fluorescein-label hIgG1. Then, salt was removed in a similar manner as for humanized anti-HM1.24 antibody-fluorescein. After determining protein concentration, it was diluted to 200 μg/ml in FACS/PBS, and BSA was added thereto to a final concentration of 0.1%.

This was set as hIgG1-fluorescein, and 1 ml aliquots thereof were stored at −80° C. Prior to use it was thawed and stored at a set temperature of 5° C. For humanized anti-HM1.24 antibody-fluorescein and hIgG1-fluorescein, samples with the number of freeze-thaw cycles being zero and one were reacted with KPMM2 cells to confirm the absence of difference in the fluorescence intensity of the cells, and to confirm that they can be stored frozen. Also, no difference in fluorescence intensity was seen in the KPMM2 cells that were reacted to hIgG1-fluorescein and the cells that were not reacted, thereby to confirm that hIgG1-fluorescein does not bind to the cells.

HM1.24 antigen-bound beads (HM-beads) were prepared in the following manner. Thus, after thawing 2 ml of soluble humanized HM1.24 antigen solution stock (0.764 mg as HM1.24 antigen), 109 μl of 1 mmol/l EZ-Link (trade mark) Sulfo-NHS-LC-Biotin (Cat. No. 21335, PIERCE) solution in water was added. The molar ratio of HM1.24 antigen to biotin was 1:2. After reacting on ice for 2 hours, 200 μl of 1 mol/l Tris buffered saline (Code No. T903, Takara Shuzo Co., Ltd.) was added to stop the biotinylation reaction.

Then, using a desalting column (SMART (trade mark) SYSTEM, Fast Desalting Column HR 10/10, Code No. 17-0591-01, Pharmacia Biotech), biotinylated HM1.24 antigen was recovered. As the solvent, PBS(-) was used. To the recovered biotinylated HM1.24 antigen, 1 ml of Streptavidin Coated Carboxylated Microspheres, 6.0 Micron (1.25% Solids-Latex, Cat. No. 24158, Polysciences) was added, and reacted at room temperature for 1 hour. After washing twice with FACS/PBS, it was suspended in 20 ml of FACS/PBS. This was set as HM-beads, and 40 μl aliquots thereof were stored at −80° C., and thawed immediately prior to use.

HM-beads with the number of freeze-thaw cycles being zero and one were reacted with humanized anti-HM1.24 antibody-fluorescein and hIgG1-fluorescein, and analyzed by flow cytometry to confirm the two exhibit equal fluorescence intensity, and it was confirmed that HM-beads can be stored frozen. Also, the beads that were reacted to hIgG1-fluorescein and the beads that were not reacted exhibited the same fluorescence intensity, confirming that the antibody does not non-specifically bind to them.

(2) Flow Cytometric Analysis and the Analytical Method

About $0.5-1\times10^6$ cells were suspended in 60 μl of the Blocking Buffer and were allowed to stand on ice for 15 minutes. After standing, 20 μl of humanized anti-HM1.24 antibody-fluorescein, hIgG1-fluorescein or FACS/PBS were added. Furthermore, 20 μl of FACS/PBS was added to make a total volume of 100 μl, and then reacted on ice for 30 minutes. In the case of HM-beads, 20 μl of beads were suspended in 60 μl of Blocking Buffer, allowed to stand on ice for 15 minutes. Then 20 μl of humanized anti-HM1.24 antibody-fluorescein or hIgG1-fluorescein was added and reacted on ice for 30 minutes.

After the reaction, these cells and beads were washed twice in FACS/PBS, and suspended in 1 ml of FACS/PBS, and then subjected to flow cytometry. The flow cytometer used was EPICS XL (BECKMAN COULTER) or EPICS ELITE (BECKMAN COULTER). When the ratio of dead cells in the sample was high, the live cell population was gated by forward scatter (FS) vs side scatter (SS) histogram. Dead cells were confirmed by PI staining.

When monocytes in the PBMC were identified, 20 Al of PE-labelled anti-CD14 antibody (Cat. No. 347497, Becton Dickinson) was added to make a total volume of 100 μl. When myeloma cells in the BMMNC were identified, 20 μl of PE-labelled anti-CD38 antibody (CD38PE, Cat. No. 347687, Becton Dickinson) was added to make a total volume of 100 μl (FIG. 1 and Table 1).

TABLE 1

Samples used in BMMNC staining

| | AHM-fluorescein | hIgG1-fluorescein | non-fluorescein Ab | CD38PE |
|---|---|---|---|---|
| HM-beads | + | − | − | − |
| HM-beads | − | + | − | − |
| BMMNC | + | − | − | + |
| BMMNC | − | + | − | + |
| BMMNC | − | − | + | + |
| SPHERO-beads | − | − | − | − |

When BMMNC is determined, flow cytometric instruments were adjusted as follows. Thus, RPMI8226 cells were adjusted with humanized anti-HM1.24 antibody-fluorescein alone ($1\times10^6$ cells, a final volume of 1 ml, this was set as A), CD38PE alone ($1\times10^6$ cells, a final volume of 1 ml, this was set as B), or without adding antibody ($2\times10^6$ cells, a final volume of 2 ml, this was set as C). A, B, and C were mixed, and analyzed by flow cytometry.

FS was adjusted so that the cell population slightly scales out in the FS vs SS histogram. SS was adjusted so that the cell population are contained in the lower half of the histogram. In the fluorescein virsus PE histogram, PE was adjusted so that the B cell population is contained in the upper half of the PE axis. Also, fluorescein was adjusted so that the cell population A is contained in the upper ⅓ of the fluorescein axis by adjusting fluorescein. Furthermore, fluorescence correction (color compensation) (PE-% fluorescein) was performed so that the PE fluorescence intensity of the cell populations A and C becomes equal. Fluorescence correction (fluorescein-%PE) was set as 0%.

(3) Standardization of Fluorescence Intensity by Fluorescence-Labelled Beads (SPHERO-Beads)

Figure 2:
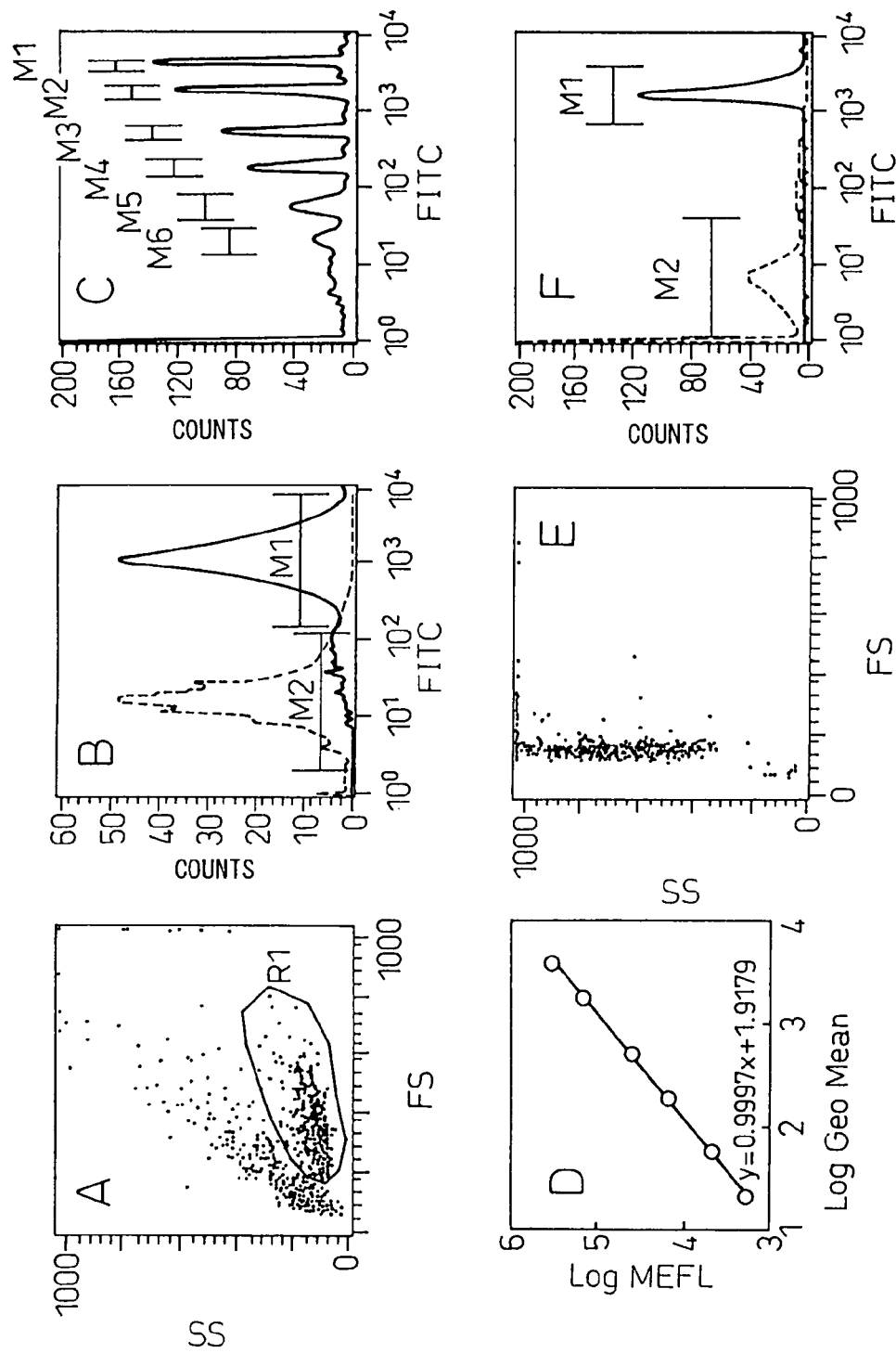
FIG. 2 is a schematic illustration of an equation of correlation between the result of fluorescence measurement by flow cytometry used for establishing a method of quantitating HM1.24 antigen and fluorescence intensity.

Using KPMM2 cells, HM1.24 antigen on the cells was determined. First, after KPMM2 cells were incubated with humanized anti-HM1.24 antibody-fluorescein and hIgG1-fluorescein, fluorescence intensity was measured using a flow cytometer and a Mean fluorescence intensity was obtained from the fluorescein histogram (B of FIG. 2). When a mean of fluorescence intensity for a cell population is obtained, two types of values, the Mean and the Geo Mean, can be calculated. They differ in the graduating of fluorescence intensity at calculation of the mean.

The Mean uses a log scale for calculation of fluorescence intensity, whereas the Geo Mean is calculated based on the resolution (1024) of graduation. Thus, more precise means of fluorescence intensity can be obtained by the Mean, whereas values close to the average position of the cell population can be obtained as the Geo Mean. Thus, when Geo Mean of fluorescence intensity of KPMM2 cells was determined, it was 1114.97 for the cells that were allowed to react with humanized anti-HM1.24 antibody-fluorescein, and 17.28 for the cells that were allowed to react with hIgG1-fluorescein. In order to determine fluorescence intensity specific for HM1.24 antigen, the difference (1097.69) of these Geo Means were calculated, the log value (Log Geo Mean, 3.04) thereof was further calculated, which was considered the fluorescence intensity of KPMM2 cells.

Since fluorescence intensity obtained by a flow cytometer is a relative value, in the case where an amount of expressed HM1.24 antigen is quantifated data must be standardized using a substance having a known fluorescence intensity. Thus, using SPHERO-beads as a standard, fluorescence intensity of cells was standardized. First, a drop of SPHERO-beads was added to FACS/PBS and a fluorescein histogram was determined (C of FIG. 2). The logarithm (Log Geo Mean) of Geo Mean for each peak was calculated, and log MEFL values were plotted against Log Geo Mean values to make a standard curve (D of FIG. 2).

By setting Log Geo Mean as x and log MEFL as y, the relation is expressed in y=0.9997x+1.9179, and by substituting the Log Geo Mean (3.04) of KPMM2 cells for x, a log MEFL value of 4.96 was obtained. Furthermore, in 14 measurements on different days and at different times, log MEFL values were 4.85, 4.95, 4.92, 4.95, 4.96, 4.90, 4.94, 4.96, 4.95, 4.92, 4.94, 4.89, 4.91, and 4.93, indicating that variation is very small. The above result made it possible to standardize the amount expressed of HM1.24 antigen on the surface of cells as log MEFL.

When fluorescence intensity is to be standardized by SPHERO-beads, a positive control substance is needed for quality control of the assay system and reagents. Thus, beads (HM-beads) to which a given amount of HM1.24 antigen has been bound were prepared (see the above test procedure), then reacted to humanized anti-HM1.24 antibody-fluorescein or hIgG1-fluorescein, and then log MEFL values were determined. As a result, the same results were obtained on different days and different instruments (Table 2). Furthermore, when another lot of HM-beads was determined four times on different days and times, log MEFL values were 5.09 (F of FIG. 2), 5.07, 5.11, and 5.13, indicating that variation is very small.

TABLE 2

Log MEFL values of HM-beads determined using different instruments on different days and times

| Date | Instrument | Log Geo Mean | Log MEFL |
| --- | --- | --- | --- |
| Apr 12, 2000 | EPICS XL* | 2.78 | 4.91 |
| Apr 21, 2000 | EPICS XL* | 2.72 | 4.88 |
| Apr 12, 2000 | FACScan* | 2.35 | 4.90 |
| Apr 21, 2000 | FACScan* | 2.32 | 4.86 |
| Apr 14, 2000 | EPICS XL** | 2.87 | 4.88 |

Figure 3:
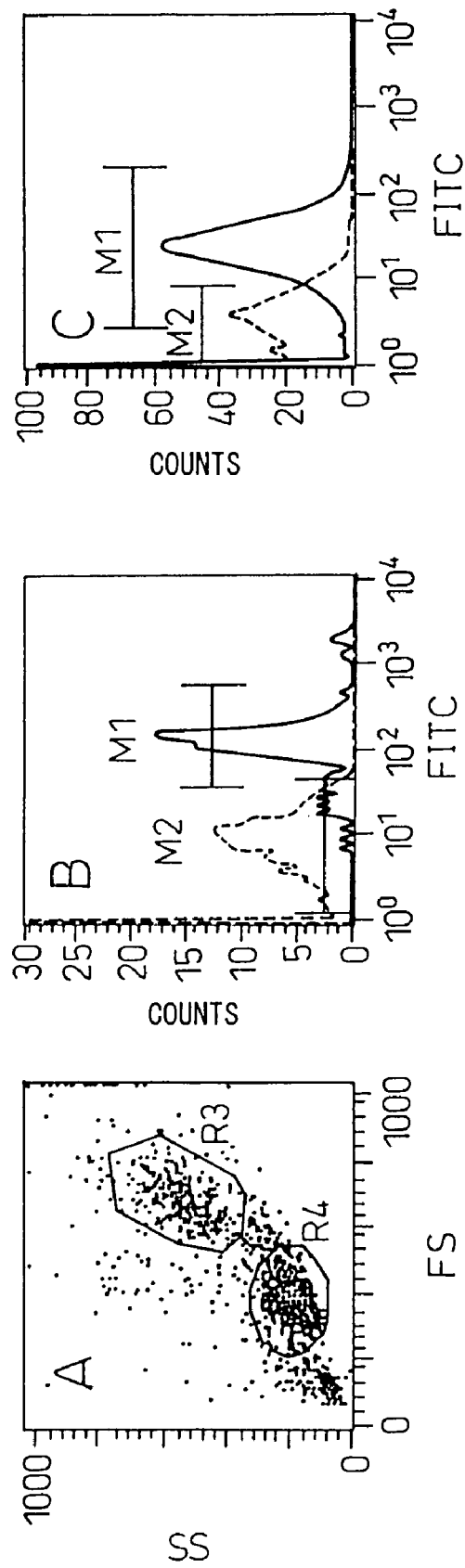
FIG. 3 is a schematic illustration of flow cytometry that determined the expression of HM1.24 antigen in monocytes and lymphocytes.

*Chugai Pharmaceutical Co., Ltd., Fuji Gotenba Research Institute
**Tokushima University, School of Medicine (4) Result (4-1) PBMC of Normal Healthy Subjects Using the assay system constructed by the above method, HM1.24 antigen in monocytes and lymphocytes was quantitated (FIG. 3). Using PBMC samples prepared from the peripheral blood of normal healthy volunteers, monocytes and lymphocytes were identified by the FS vs SS histogram. In four runs of an experiment on two normal healthy volunteers, log MEFL values for monocytes were 4.00, 3.97, 3.96 (these are for volunteer A), and 3.90 (volunteer B), whereas log MEFL values for lymphocytes were 3.25, 3.16, 3.20 (these are for volunteer A), and 3.04 (volunteer B). Thus, even when the amount of HM1.24 antigen is small, measured values with small variation could be obtained.

(4-2) Hematopoietic Tumor Cell Lines

Figure 4:
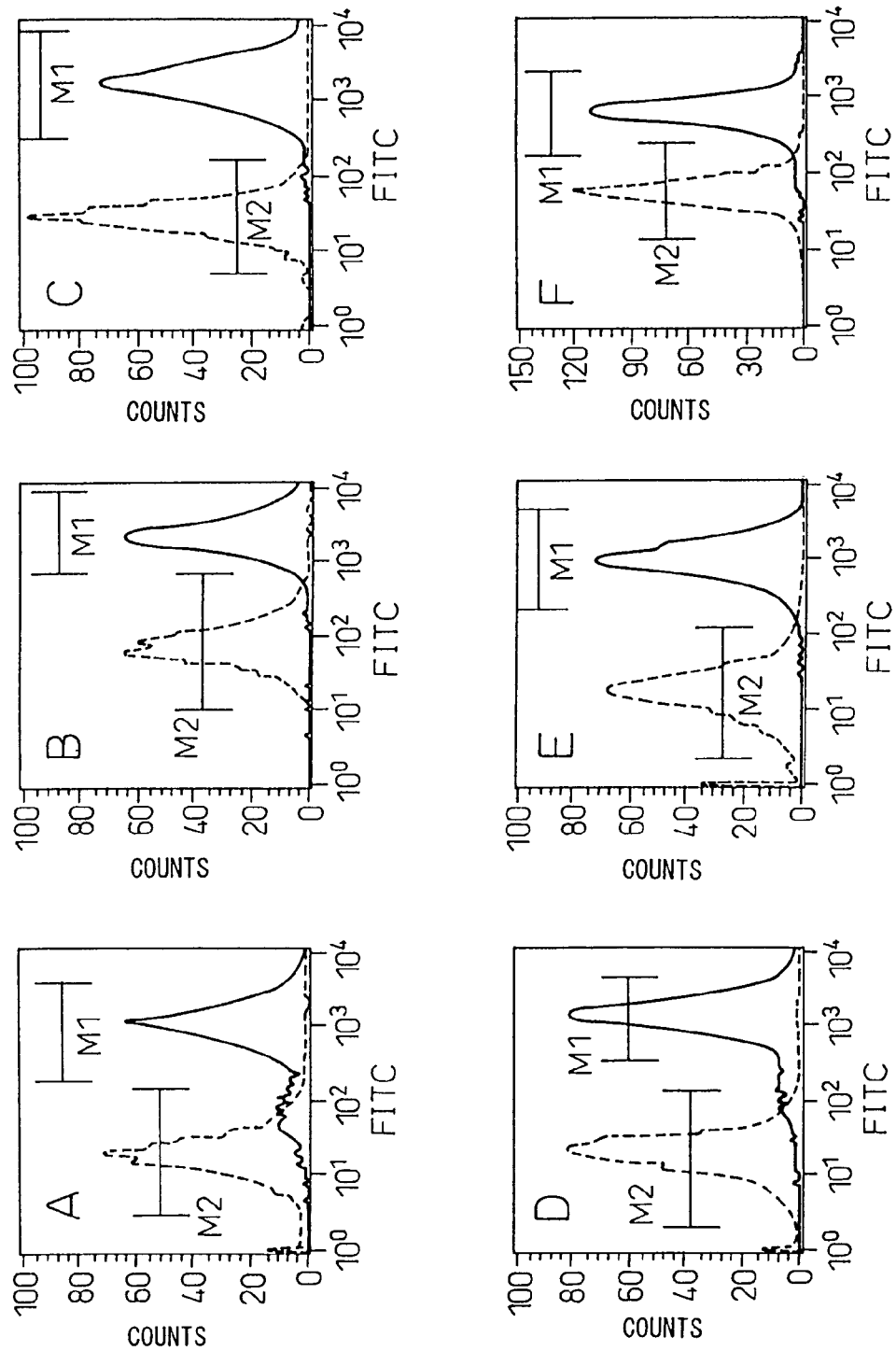
FIG. 4 is a schematic illustration of flow cytometry that determined the expression of HM1.24 antigen in various human cell lines.

As hematopoietic tumor cell lines, human myeloma cell lines (KPMM2, RPMI8226, U266B1), a plasma cell leukemia cell line (ARH-77), a B lymphoblast cell line (IM-9), a plasmacytoma cell line (HS-Sultan) were used. The amount expressed of HM1.24 antigen in these cells was quantitated (FIG. 4). As a result, RPMI8226 exhibited the highest value (log MEFL: 5.21), followed by U266B1 (log MEFL: 5.08), ARH-77 (5.02), KPMM2 (4.90), IM-9 (4.85), and HS-Sultan (4.63). It was demonstrated that HM1.24 antigen is more highly expressed in these hematopoietic tumor cell lines compared to PBMC.

(4-3) Measurement of Myeloma Cells Derived from Patients

Figure 5:
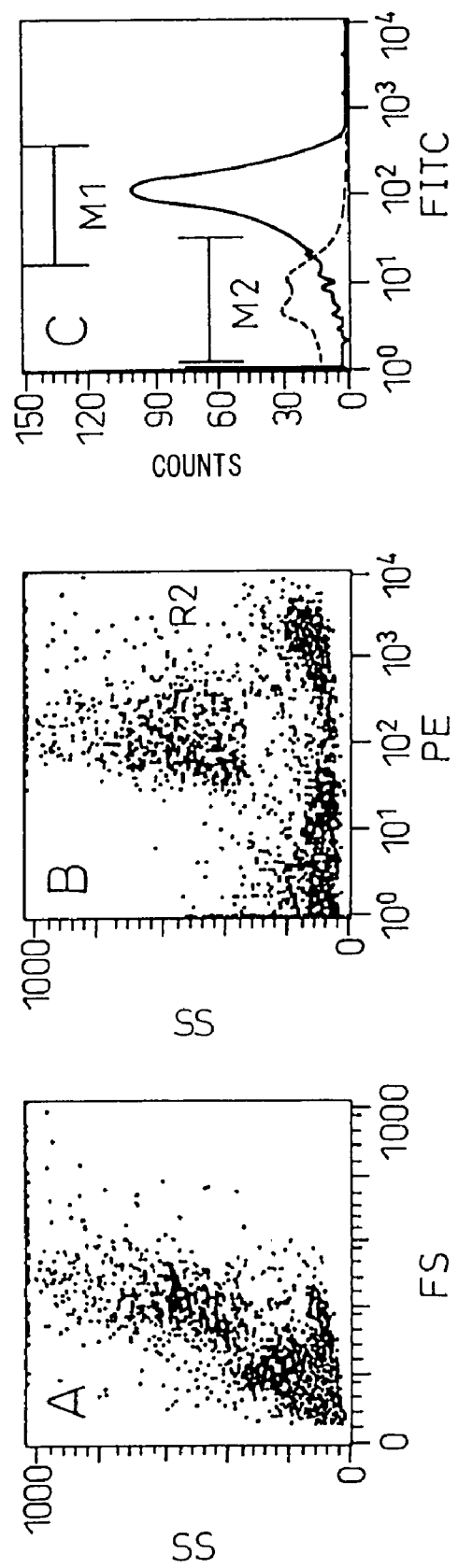
FIG. 5 is a schematic illustration of flow cytometry that determined the expression of HM1.24 antigen in myeloma cells derived from patients with myeloma.

Myeloma cells are expressing CD38 at high levels, and this can be used as a marker for identification. Thus, BMMNC prepared from bone marrow puncture samples of myeloma patients was stained with CD38PE, and CD38-strong positive cells by the PE vs SS histogram were considered myeloma cells (B of FIG. 5). The measurement of the amount expressed of HM1.24 antigen in the cells gave a log MEFL value of 3.98 (C of FIG. 5).

Figure 6:
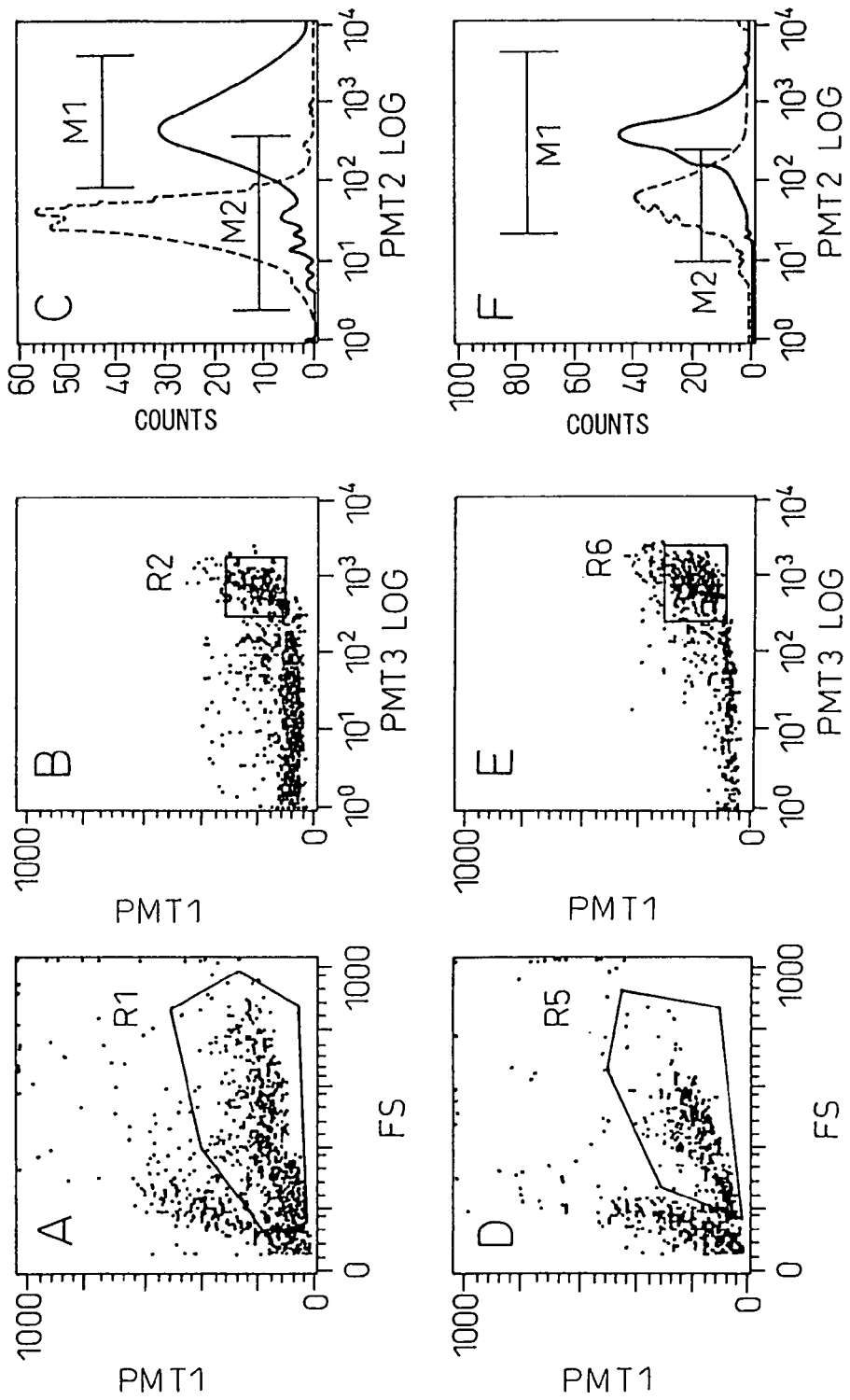
FIG. 6 is a schematic illustration of flow cytometry that determined the expression of HM1.24 antigen in myeloma cells derived from patients with myeloma.
Figure 7:
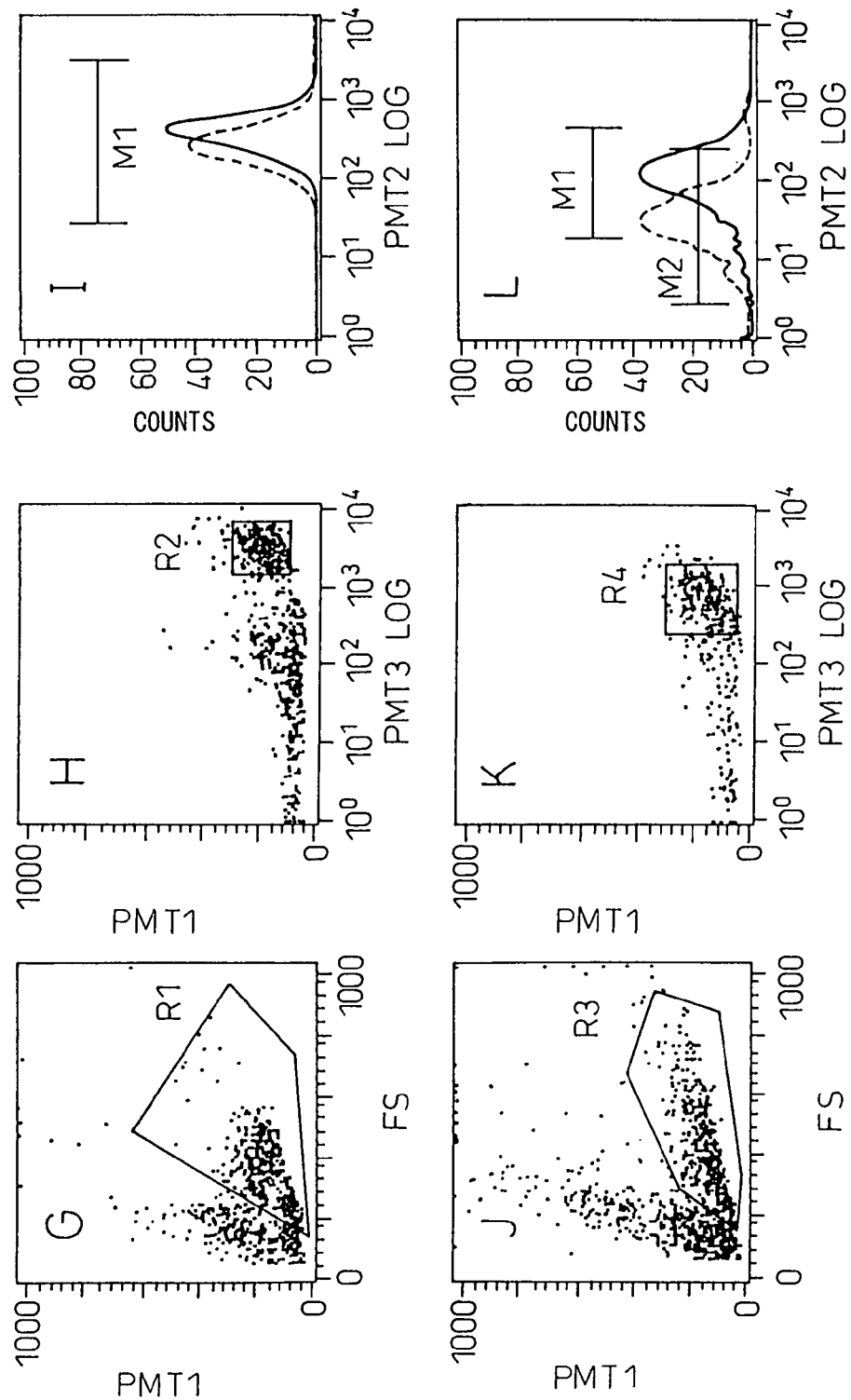
FIG. 7 is a schematic illustration of flow cytometry that determined the expression of HM1.24 antigen in myeloma cells derived from patients with myeloma.

It was investigated whether frozen cells give similar results. When a total of four samples of frozen BMMNC obtained from two different facilities were measured in a similar manner, all tumor cells expressed HM1.24 antigen, and log MEFL was calculated as 4.69, 4.51, 4.22, and 4.11 (FIG. 6 and FIG. 7). It was confirmed that, even in frozen cells, HM1.24 antigen in the tumor cells from patients can be quantitated.

Example 2

Determination of Amount Expressed of HM1.24 Antigen and ADCC Activity

Materials for Experiment

[125I]-labelled humanized anti-HM1.24 antibody ( 125I-humanized anti-HM1.24 antibody) was prepared using IODINE-125 (SODIUM IODIDE IN pH10 SODIUM HYDROXIDE), Cat. No. NEZ033A, (NEN Life Science Products, Inc.) and Chloramine T (Cat. No. 032-02182, Wako Pure Chemical Industries, Ltd.) according to supplier's instructions.

$^{125}$I-humanized anti-HM1.24 antibody (antibody concentration 9.47 µg/ml, specific radioactivity 0.0912 MBq/µg, radiochemical purity 96.1%) contains as solvent PBS(-) containing 0.05% Tween 20 (Tokyo Kasei Kogyo Co., Ltd.), and stored at 4° C.

Human tumor cell lines used are KPMM2 (International Deposit Number FERM BP-7419), RPMI8226 (ATCC CCL-155), U266B1 (ATCC TIB-196) (these are multiple myeloma), ARH-77 (ATCC CRL-1621) (plasma cell leukemia), IM-9 (ATCC CCL-159) (B lymphoblast), HS-Sultan (ATCC CRL-1484) (plasmacytoma), CCRF-SB (ATCC CCL-120) (acute lymphoblastic leukemia (B lymphoblastoid)), EB-3 (ATCC CCL-85) (Burkitt's lymphoma), CCRF-CEM (ATCC CCL-119) (acute lymphoblastic leukemia (T cell)), Daudi (ATCC CCL-213) (Burkitt's lymphoma (B lymphoblast)), and MOLT-4 (ATCC CRL-1582) (acute lymphoblastic leukemia (T cell)).

HM1.24 antigen-expressing CHO cells (CHO/HM21, CHO/HM25, CHO/HM31, CHO/HM32, CHO/HM34, CHO/HM36, CHO/HM37, CHO/HM39) were prepared by the method described in Biochemical and Biophysical Research Communications 258, 583-591 (1999). Thus, a vector encoding HM1.24 antigen was transfected to CHO cells to obtain HM1.24 antigen-expressing CHO cells. The cells obtained were rendered single cells and cultured to establish 60 strains of cell lines that exhibit a single amount of expression. From these established cell lines, a plurality of cell lines were selected having different expressed amounts of HM1.24 antigen.

For cultivation of CHO cell lines, a-MEM medium (Cat. No. 11900, GIBCO BRL) (hereinafter referred to as 10% FBS/αMEM medium) supplemented with 10% FBS, 500 µg/ml Geneticin (Cat. No. 10131-035, GIBCO BRL), and 0.1 mg potency/ml kanamycin sulfate was used.

The target cell suspension for use in the measurement of ADCC activity were prepared immediately prior to use. In the case of CHO cells, the cells were cultured in a 60 mm dish for 2-3 days and the number of cells per dish was rendered $1 \times 10^6$ cells. The cell count was confirmed by a dish that is not used in the experiment. After aspirating the supernatant, 500 µl of 10% FBS/αMEM medium and 5.55 MBq of chromium-51 (Code No. CJS4, Amersham Pharmacia Biotech) were added, and cultured in a 5% carbon dioxide incubator at 37° C. for 1 hour. The cells were washed twice in 10% FBS/αMEM medium and once in PBS(-). The cells were scraped from the dish using 300 µl of EDTA (0.02% EDTA solution, Code No. 382-14, Nacalai Tesque Inc.), and the cell density was adjusted to $2 \times 10^5$/ml in 10% FBS/RPMI medium to prepare a target cell suspension.

For other cell lines, $1 \times 10^6$ cells were centrifuged, and the cell pellet was suspended in about 200 µl of 10% FBS/RPMI medium and 5.55 MBq of chromium-51 (Code No. CJS4, Amersham Pharmacia Biotech), and then cultured in a 5% CO2 incubator at 37° C. for 1 hour. After the cells were washed three times in 10% FBS/RPMI medium, the cell density was adjusted to $2 \times 10^5$/ml in 10% FBS/RPMI medium to prepare a target cell suspension.

Other materials used, that are not specifically mentioned such as peripheral blood mononuclear cells (PBMC) derived from normal healthy subjects, are the same as those used in Example 1.

(2) Determination of the Amount of HM1.24 using 125I-Humanized Anti-HM1.24 Antibody $^{125}$I-humanized anti-HM1.24 antibody was diluted to a concentration of 1.38 nmol/l in 10% FBS/RPMI medium to prepare a $^{125}$I-humanized anti-HM1.24 antibody solution. Humanized anti-HM1.24 antibody that is not labelled with a radioisotope was diluted to a concentration of 1.38, 4.13, 9.63, 20.6, 42.6, and 1375 nmol/l in 10% FBS/RPMI medium to prepare a nonlabelled humanized anti-HM1.24 antibody solution. After CHO cells were washed in 10% FBS/RPMI medium, CHO/HM36 and CHO/HM39 were adjusted to a cell concentration of $1.1 \times 10^6$/ml, CHO/HM21 to $4.4 \times 10^6$/ml, CHO/HM31 and CHO/HM32 to $5.5 \times 10^6$/ml, and 200 µl of them was aliquoted to 1.5 ml microtubes. Ten µl each of $^{125}$I-humanized anti-HM1.24 antibody solution and the non-labelled humanized anti-HM1.24 antibody solution was added thereto, and reacted on ice for 3 hours.

During this period, they were stirred every 30 minutes. From each tube, 200 µl aliquots were taken and slowly layered on a 0.4 ml microtube (Assist tube, Cat. No. 72.701, K. K. Ashisuto) to which 150 µl of FBS had previously been dispensed. After centrifuging (10,000 rpm, 3 minutes, 4° C.) the microtube, it was frozen at a set temperature of −80° C. Antibody bound to the cells are fractionated to the cell pellet, and free antibody is fractionated to the supernatant, the cell pellet and the supernatant were separated by cutting the microtube. Each radioisotope was counted by a gamma counter (COBRA II AUTO-GAMMA, MODEL D5005, Packard Instrument Company), and the radioactivity of the cell pellet was set as Bound (cpm) and the radioactivity of the supernatant was set as Free (cpm).

Antibody was added as follows.

$^{125}$I-humanized anti-HM1.24 antibody was added to a final concentration of 0.0625 nmol/l. The total antibody concentration combining $^{125}$I-humanized anti-HM1.24 antibody and nonlabelled humanized anti-HM1.24 antibody was set as Total (nmol/l). Nonlabelled humanized anti-HM1.24 antibody was added so that the concentration of Total (nmol/l) is (1) 2 nmol/l, (2) 1 nmol/l, (3) 0.5 nmol/l, (4) 0.25 nmol/l, (5) 0.125 nmol/l, and (6) 0.0625 nmol/l. Nonlabelled humanized anti-HM1.24 antibody at a 1000-fold concentration of $^{125}$I-humanized anti-HM1.24 antibody (final concentration 0.0625 nmol/l) was added to prepare the cold inhibition ((7)). The experiment was carried out in duplicate. Calculation was made assuming the molecular weight of antibody is 148 kDa.

The Bound (cpm) of the cold inhibition ((7)) was set as Non Specific Bound (cpm), and the Bound (cpm) of (1) to (6) from which the Non Specific Bound (cpm) was subtracted was set as Specific Bound (cpm).

The number of binding sites of humanized anti-HM1.24 antibody was calculated by the Scatchard analysis. Thus, the concentration B (nmol/l) of antibody that specifically bound to the antigen was calculated from Total (nmol/l)×Specific Bound/(Bound+Free). The concentration F (nmol/l) of free antibody was calculated from Total (nmol/l)×Free/(Bound+Free).

If the concentration of total binding sites is Bmax (nmol/l) and the dissociation constant of humanized anti-HM1.24 antibody is Kd (nmol/l), then the following equation of relation holds $$B/F = -(1/Kd)B + (1/Kd)B\text{max}.$$

B/F was taken on the Y axis and B was taken on the X axis, and Kd was obtained from the slope, and Bmax was obtained from the X intercept. The number of binding sites of humanized anti-HM1.24 antibody per cell was calculated from Bmax. As humanized anti-HM1.24 antibody is a monoclonal antibody, the number of binding sites was calculated as the number of binding sites=the number of antigens.

(3) Chromium Release Test

Humanized anti-HM1.24 antibody and the hIgG1 solution was diluted in 10% FBS/RPMI medium to prepare an antibody solution. To a 96-well U-bottomed plate, 50 μl each of the antibody solution and the target cell suspension was added, and incubated on ice for 15 minutes. Then, 100 μl of PBMC was added as the effector cell to each well, and incubated in a 5% CO2 incubator at 37° C. for 4 hours. The final effector cells/target cells ratio (E/T) were made 50/1, 20/1, and 8/1. After centrifugation (1000 rpm, 5 minutes, 4° C.), 100 μl each of the supernatant was recovered, and radioactivity thereof was counted using a gamma counter (COBRA II AUTO-GAMMA, MODEL D5005, Packard Instrument Company). Specific chromium release rate was obtained from the following equation.

$$\text{Specific chromium release rate} = (A-C) \times 100/(B-C)$$

A is radioactivity (cpm) at each well, B is a mean value of radioactivity (cpm) in a well to which 50 μl of target cell suspension, 20 μl of 10% NP-40 aqueous solution (Nonidet (trade mark) P-40, Code No. 252-23, Nacalai Tesque Inc.), and 130 μl of 10% FBS/RPMI medium were added, and C is a mean value of radioactivity (cpm) in a well to which 50 μl of target cell suspension and 150 μl of 10% FBS/RPMI medium were added.

The test was carried out in triplicate, and means and standard errors were calculated for specific chromium release rate. Furthermore, when CHO cells were used as the target cells, the specific chromium release rate in the absence of antibody was subtracted from the specific chromium release rate in its presence to obtain an ADCC activity (%).

Also, a specific chromium release rate was determined in a well to which no effector cells were added and humanized anti-HM1.24 antibody (a final concentration of 10 μg/ml) was added, and it was confirmed that there is no direct damaging effect by humanized anti-HM1.24 antibody.

Figure 8:
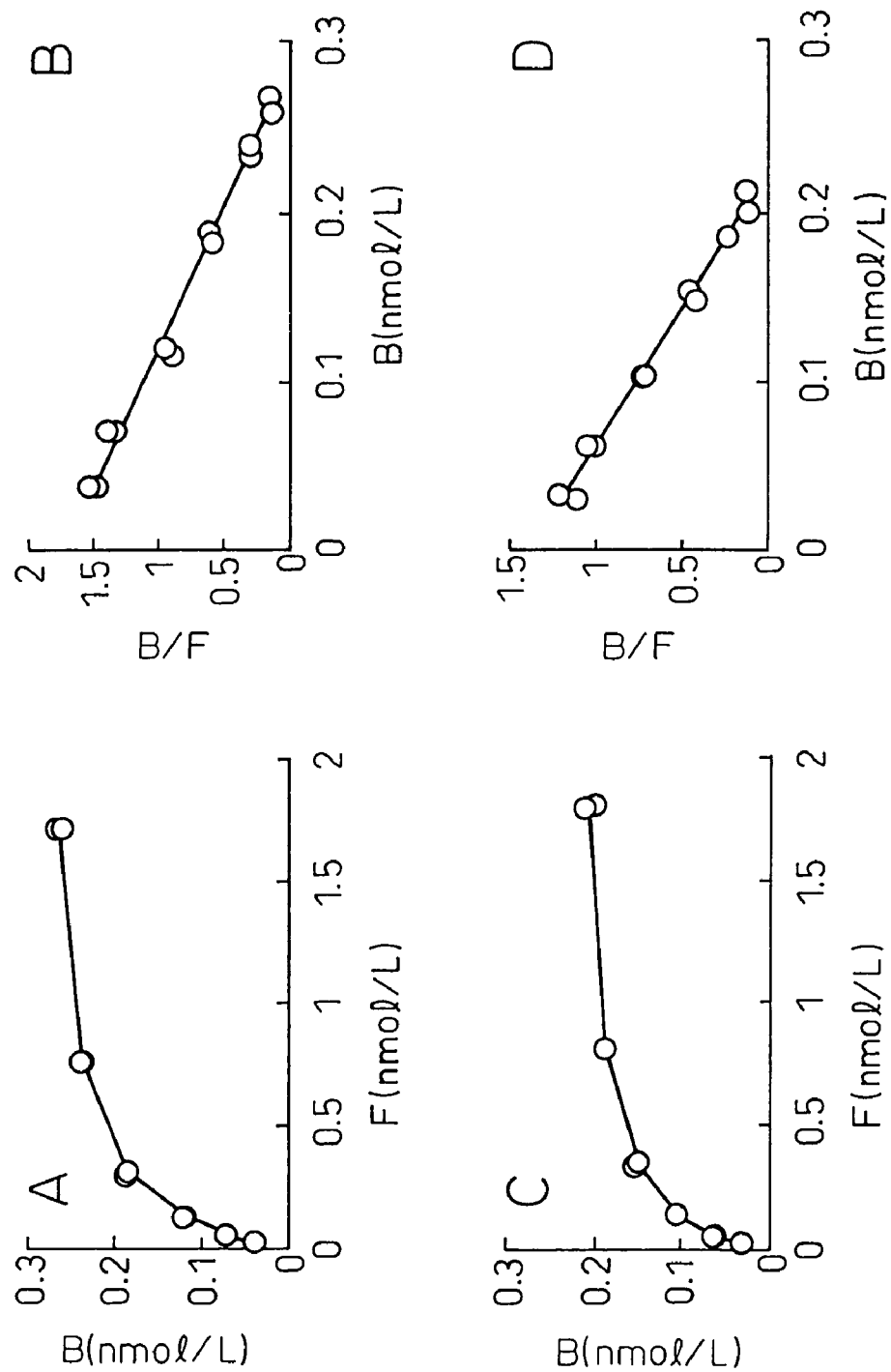
FIG. 8 is a schematic illustration of a Scatchard plot in various HM1.24 antigen-expressing CHO cell lines.
Figure 9:
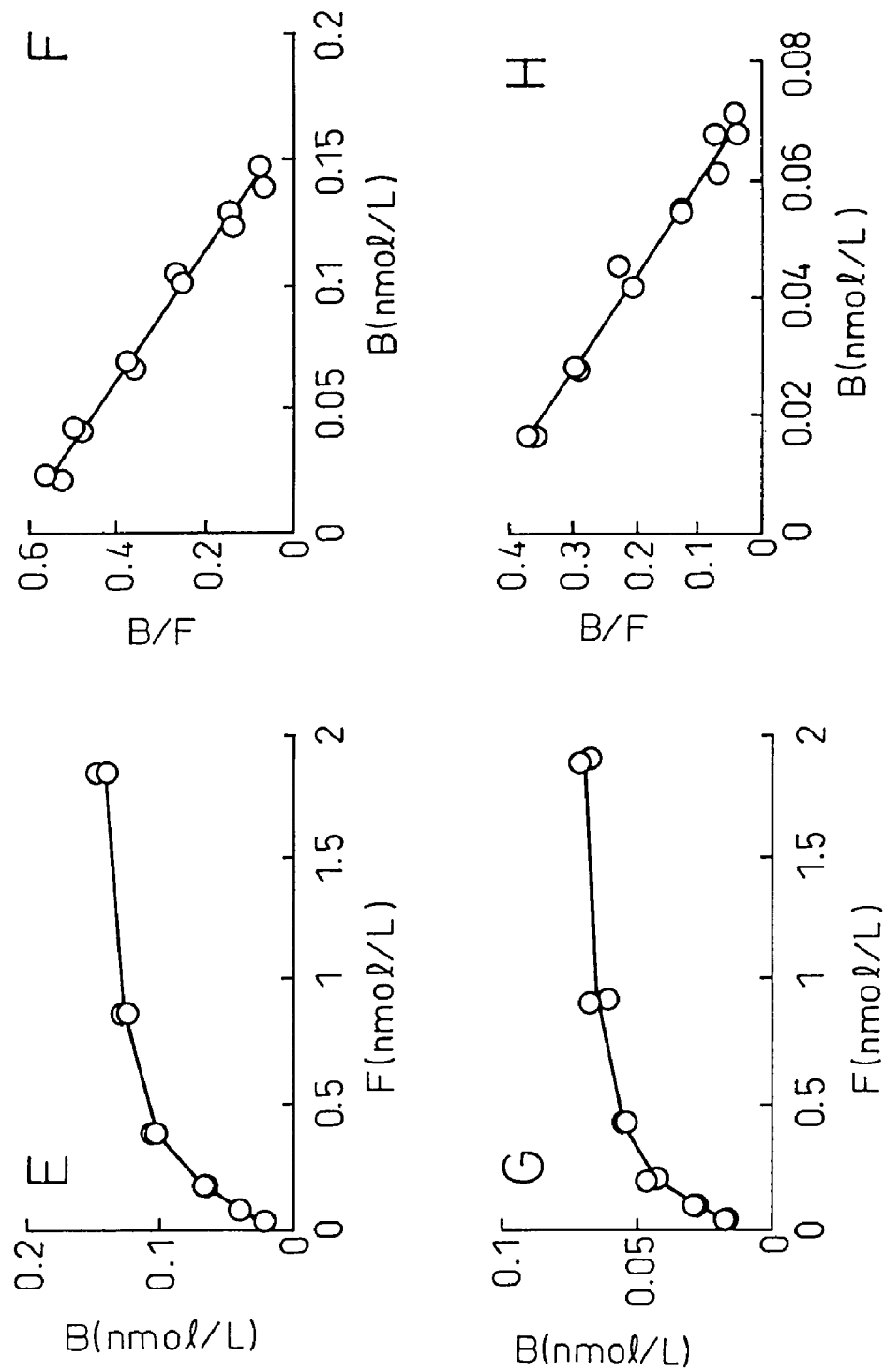
FIG. 9 is a schematic illustration of a Scatchard plot in various HM1.24 antigen-expressing CHO cell lines.
Figure 10:
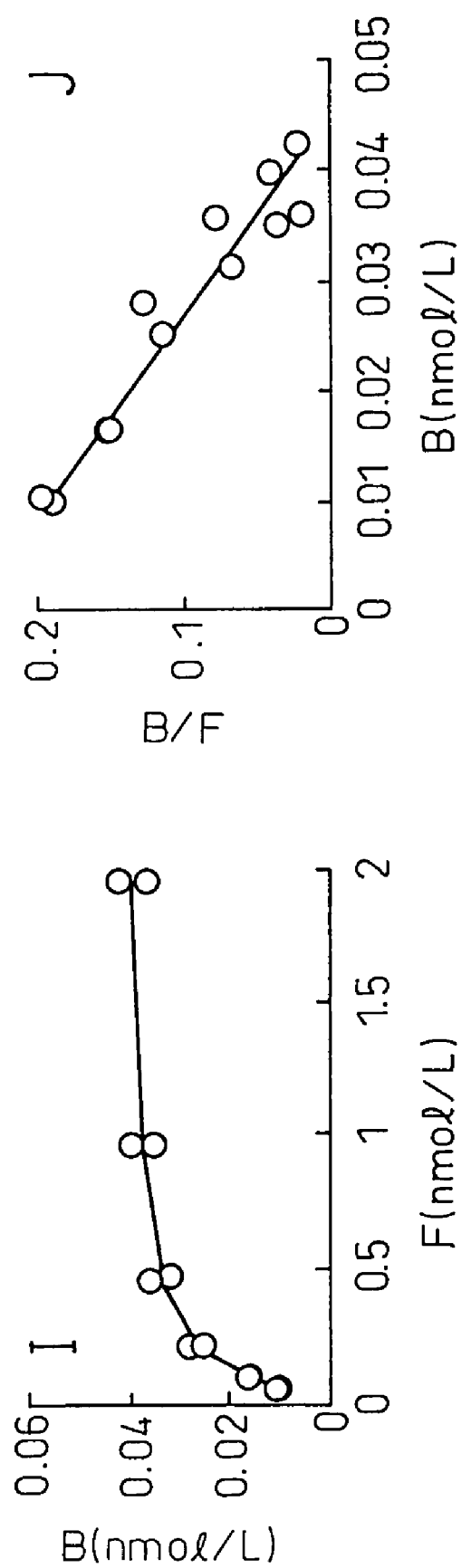
FIG. 10 is a schematic illustration of a Scatchard plot in various HM1.24 antigen-expressing CHO cell lines.
Figure 11:
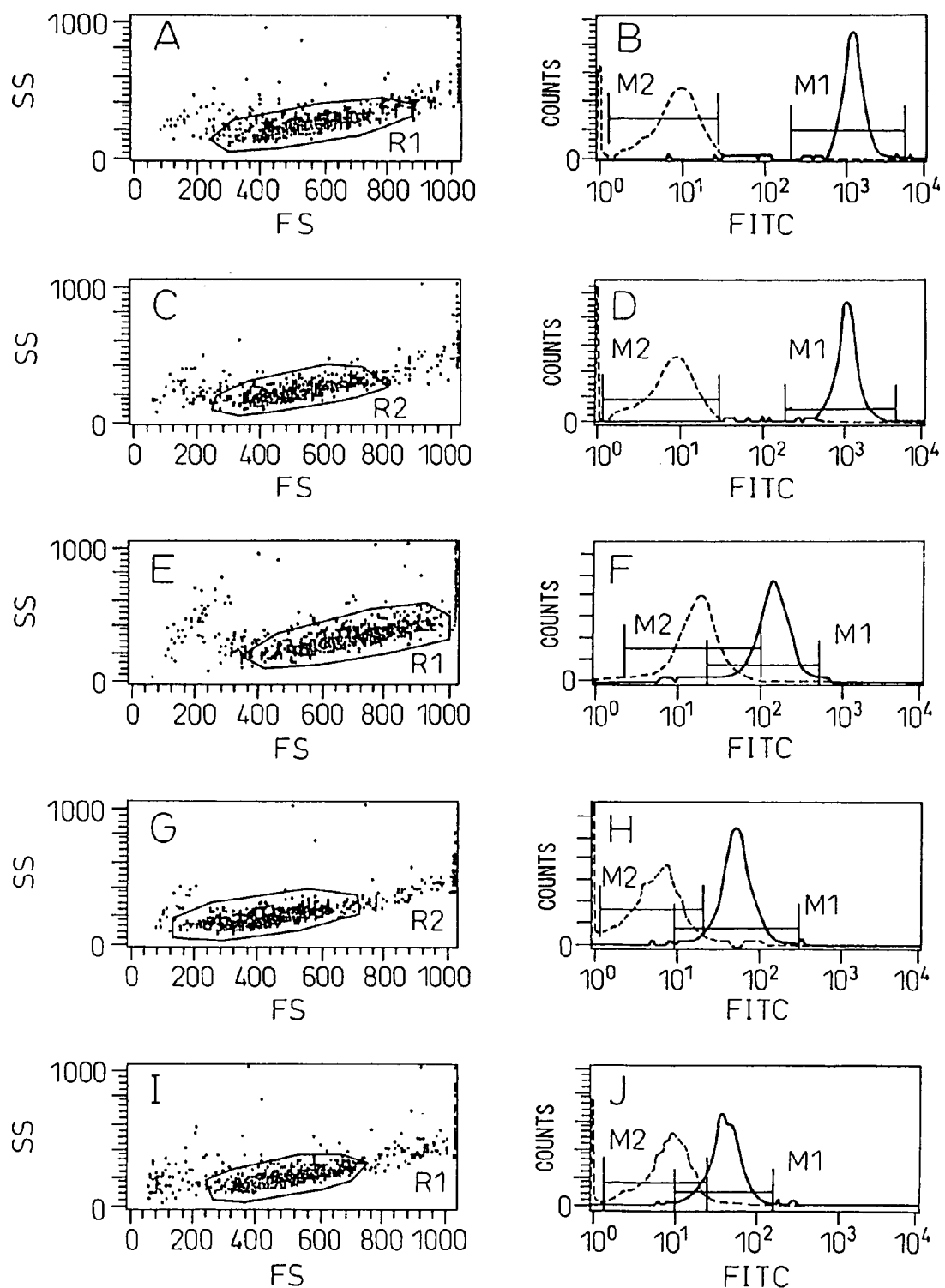
FIG. 11 is a schematic illustration of flow cytometry that determined the expression of HM1.24 antigen in various HM1.24 antigen-expressing CHO cell lines.

Result (4-1) Correlation Between Log MEFL and the Amount Expressed of HM1.24 Antigen and ADCC Activity Correlation between Log MEFL and the amount expressed of HM1.24 antigen was investigated. First, the amount expressed of HM1.24 antigen in HM1.24 antigen-expressing CHO cells was determined by a test using 125I-humanized anti-HM1.24 antibody. The amount expressed of HM1.24 antigen in five CHO cell lines, CHO/HM21, CHO/HM31, CHO/HM32, CHO/HM36, and CHO/HM39, was calculated to be $2.50 \times 10^4$, $9.14 \times 10^3$, $5.51 \times 10^3$, $1.72 \times 10^5$, and $1.35 \times 10^5$, respectively (FIG. 8 to FIG. 10). Then, for these cell lines, Log MEFL values were determined and were found to be 4.20, 3.81, 3.64, 5.17 and 5.12, respectively (FIG. 11). When Log MEFL was plotted on the x axis and the number of HM1.24 antigens on the Y axis, the relation was found to be $$Y = 2.53e^{2.15x}$$

Figure 12:
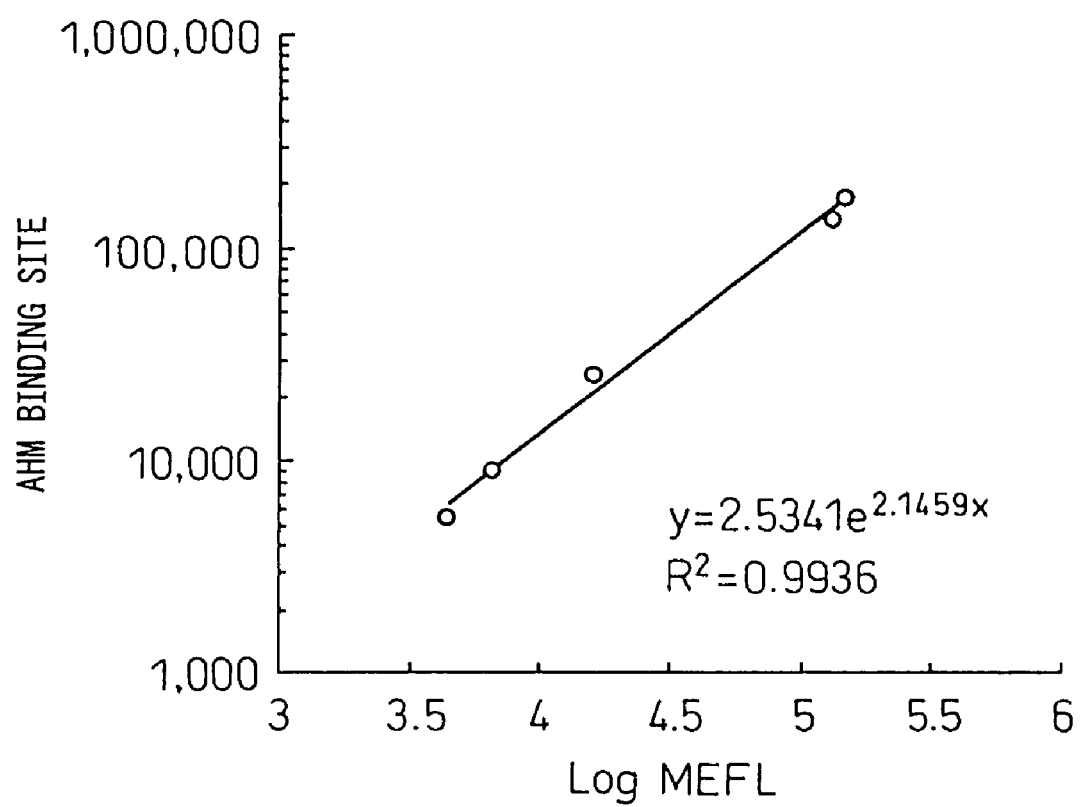
FIG. 12 is a schematic illustration showing correlation between the number of HM1.24 antigens and the log MEFL value.

(FIG. 12). The coefficient of correlation (R2) was 0.994, showing a high correlation.

Figure 13:
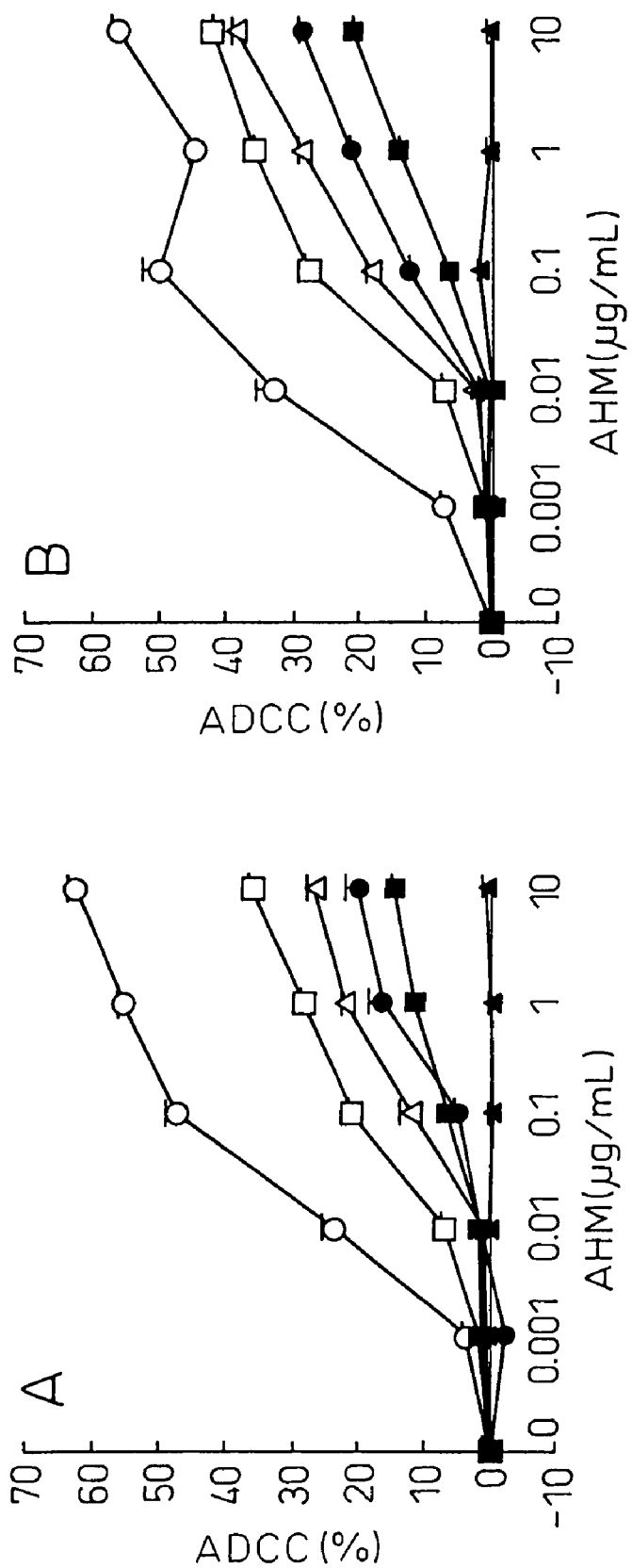
FIG. 13 is an illustration showing the ADCC activity of humanized anti-HM1.24 antibody (AHM) in various HM1.24 antigen-expressing CHO cell lines.
Figure 14:
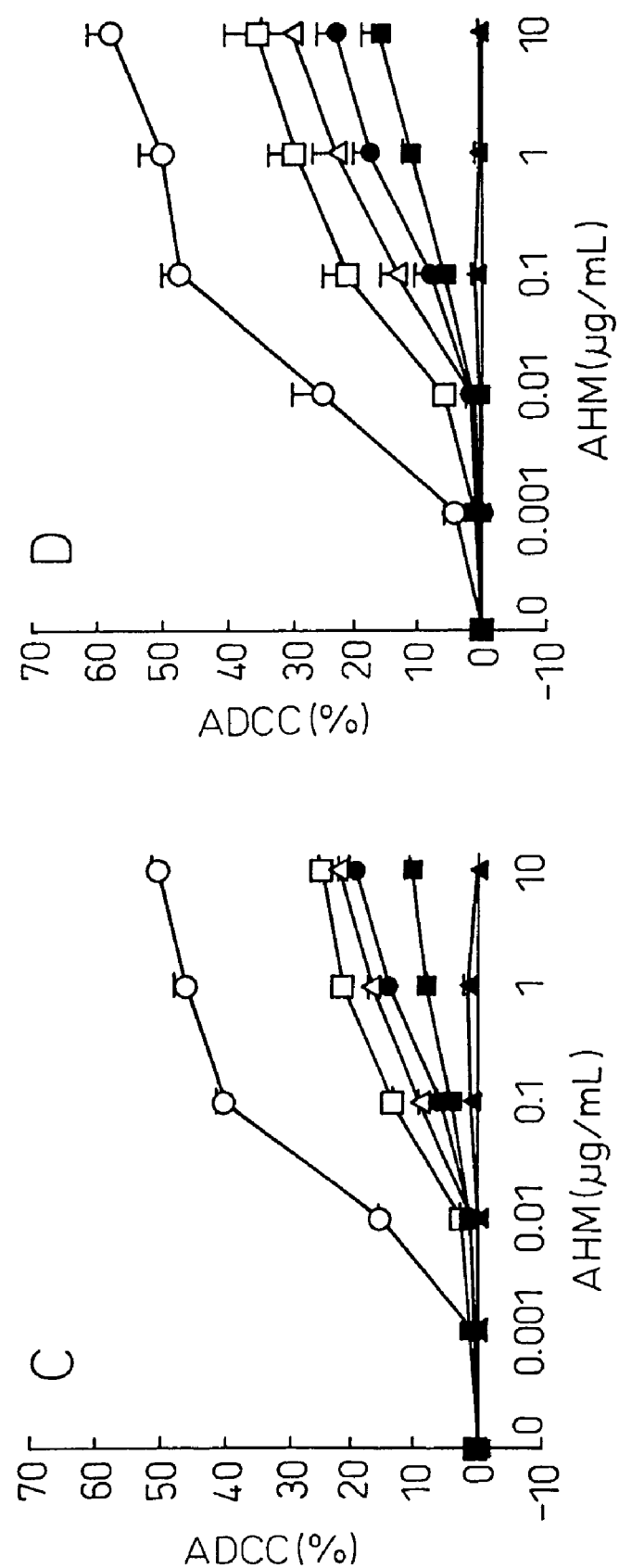
FIG. 14 is an illustration showing the ADCC activity of humanized anti-HM1.24 antibody (AHM) in various HM1.24 antigen-expressing CHO cell lines.

Then, correlation between Log MEFL and ADCC activity was investigated. First, CHO/HM21, CHO/HM25, CHO/HM31, CHO/HM34, and CHO/HM36 were used as the target cell, and the ADCC activity of humanized anti-HM1.24 antibody was determined by the chromium release test. As the effector cell, human PBMC was used and the E/T ratio was made 50/1. The experiment was carried out three times (Exp. 1, Exp. 2, Exp. 3) using the PBMC from normal healthy volunteers as the effector cell, and the mean and the standard error of three experiments were calculated (FIG. 13 and FIG. 14). As a result, for any of the CHO cells, ADCC activity was induced depending on the concentration of humanized anti-HM1.24 antibody. No ADCC activity was observed for CHO/HM37 that does not express HM1.24 antigen. For these CHO cells used as the target cells, Log MEFL was determined, and the mean and standard error of three experiments were calculated (Table 3).

TABLE 3

Log MEFL values and the number (the number of AHM binding sites) of HM1.24 antigens in various HM1.24 antigen-expressing CHO cell lines

| | Log MEFL | | | | | |
|---|---|---|---|---|---|---|
| | Exp. 1 | Exp. 2 | Exp. 3 | Mean | Standard error | AHM binding site* |
| CHO/HM36 | 5.27 | 5.30 | 5.24 | 5.27 | 0.02 | $2.11 \times 10^5$ |
| CHO/HM21 | 4.31 | 4.34 | 4.30 | 4.32 | 0.01 | $2.73 \times 10^4$ |
| CHO/HM31 | 3.82 | 3.82 | 3.78 | 3.81 | 0.01 | $9.13 \times 10^3$ |
| CHO/HM34 | 3.69 | 3.67 | 3.61 | 3.66 | 0.02 | $6.62 \times 10^3$ |
| CHO/HM25 | 3.37 | 3.32 | 3.29 | 3.33 | 0.02 | $3.25 \times 10^3$ |

*Calculated from the equation: $y = 2.53e^{2.15x}$ (x = Log MEFL, y = AHM binding site)

Figure 15:
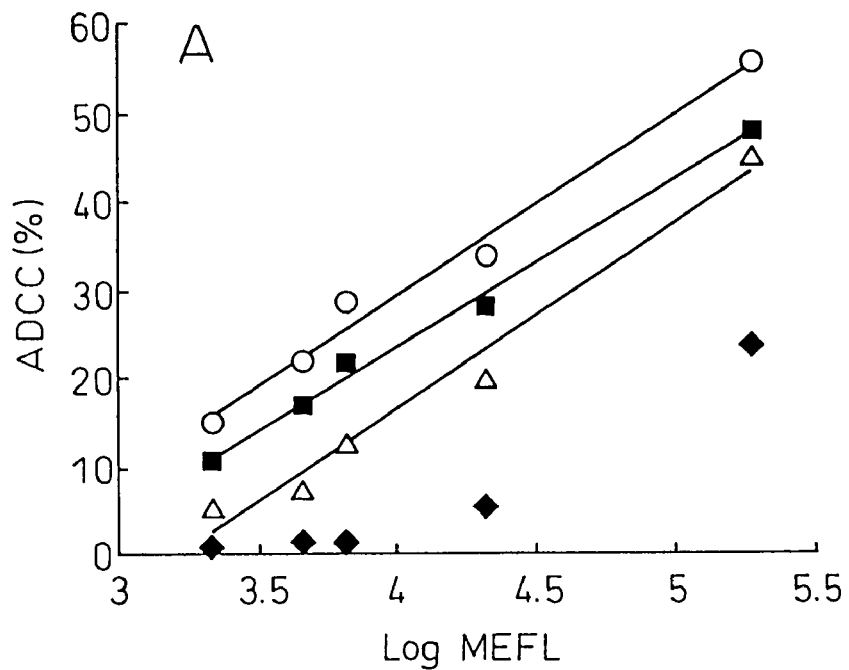
FIG. 15 is an illustration showing correlation between the amount expressed of HM1.24 antigen and ADCC activity due to humanized anti-HM1.24 antibody (AHM).
Figure 16:
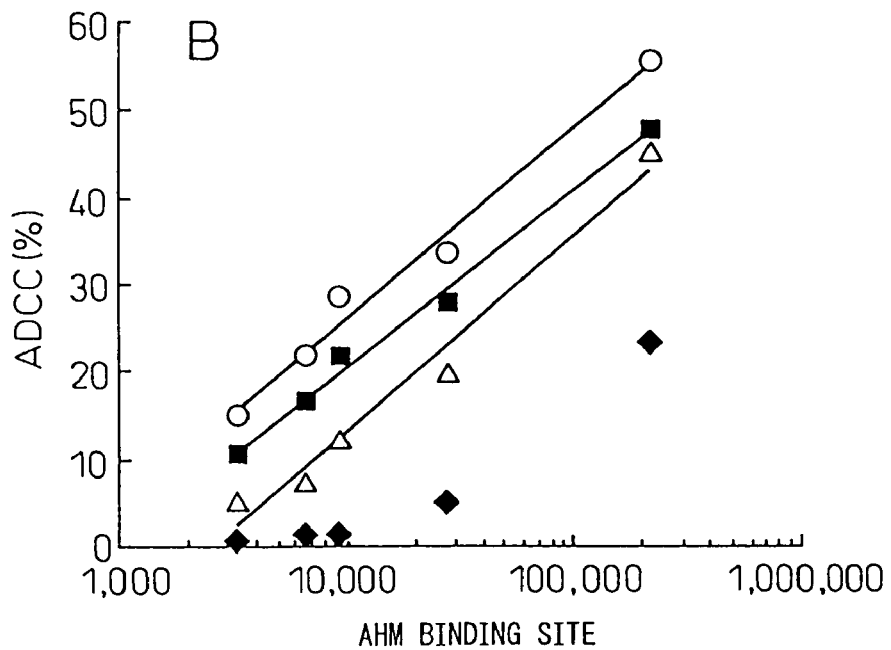
FIG. 16 is an illustration showing correlation between the amount expressed of HM1.24 antigen and ADCC activity due to humanized anti-HM1.24 antibody (AHM).
Figure 17:
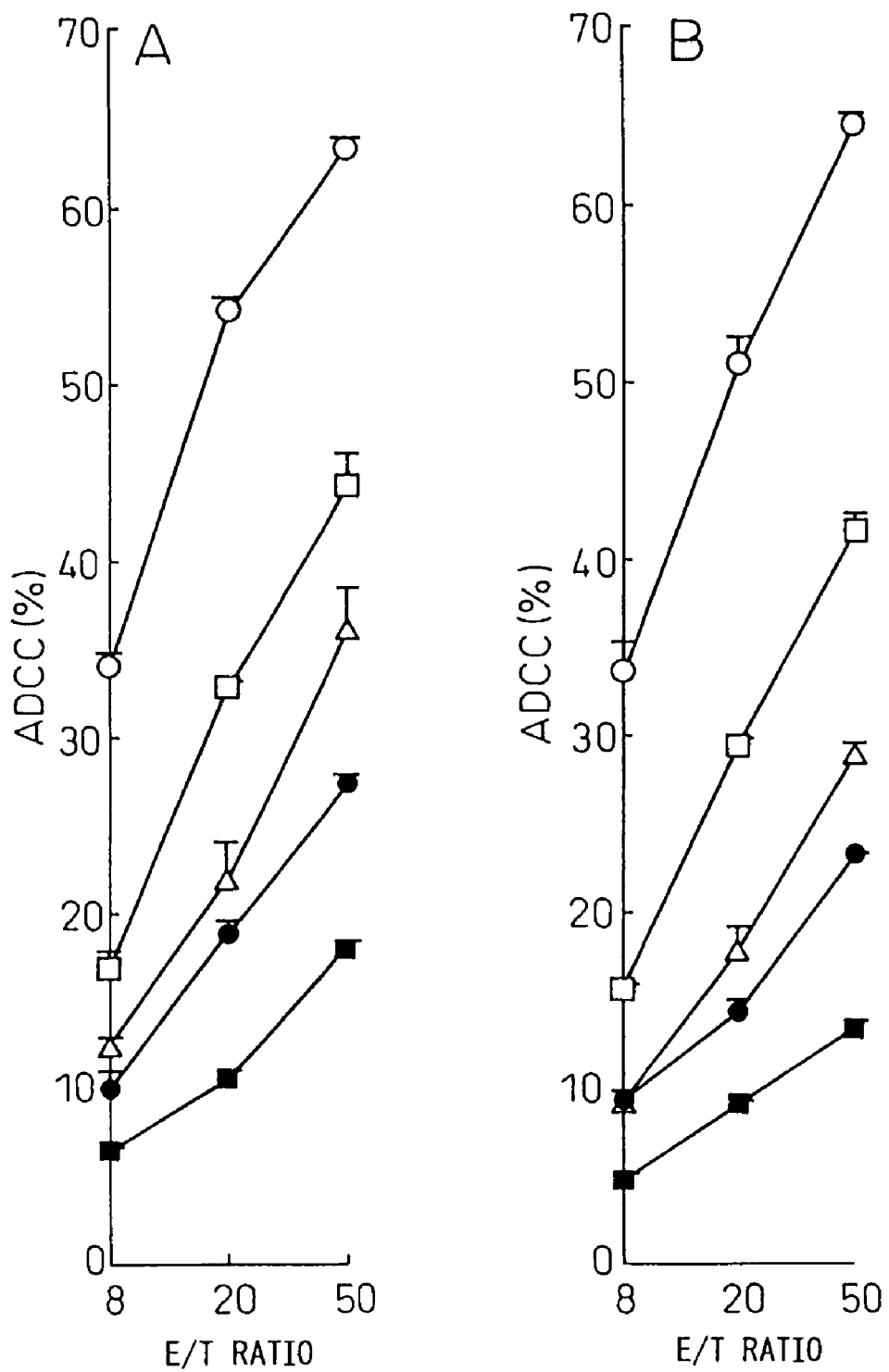
FIG. 17 is an illustration showing changes in ADCC activity due to humanized anti-HM1.24 antibody (AHM) accompanied by changes in the E/T ratio in various HM1.24 antigen-expressing CHO cell lines.
Figure 18:
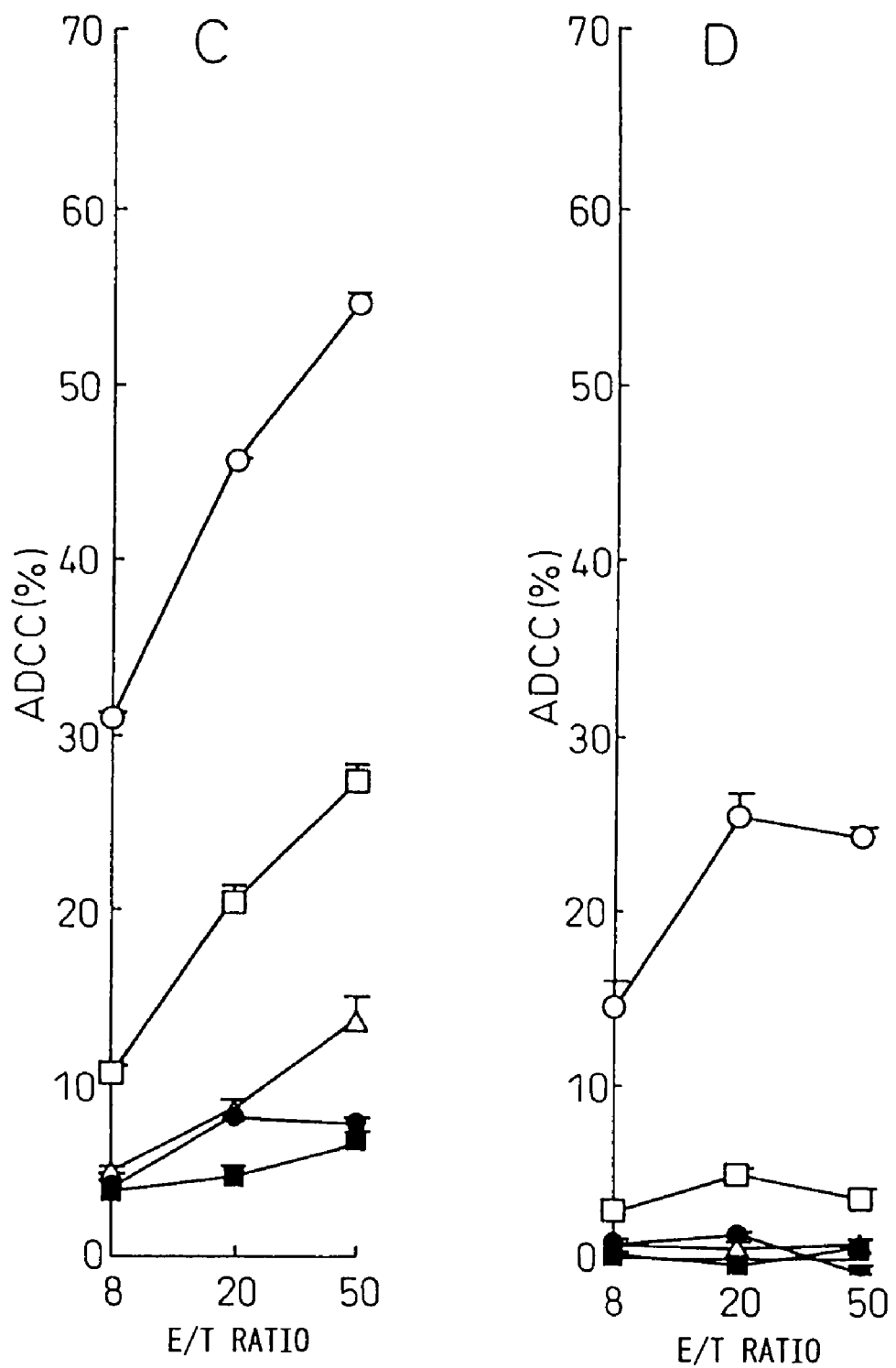
FIG. 18 is an illustration showing changes in ADCC activity due to humanized anti-HM1.24 antibody (AHM) accompanied by changes in the E/T ratio in various HM1.24 antigen-expressing CHO cell lines.

The amounts expressed of HM1.24 antigen for CHO cells were, in a decreasing order, CHO/HM36 (Log MEFL: 5.27), CHO/HM21 (4.32), CHO/HM31 (3.81), CHO/HM34 (3.66), and CHO/HM25 (3.33). From the equation in FIG. 12, the number of HM1.24 antigens was calculated (Table 3). When ADCC activity for each CHO cells was plotted against Log MEFL, high correlation was observed for humanized anti-HM1.24 antibody at concentrations of 10 μg/ml, 1 μg/ml, and 0.1 μg/ml (FIG. 15 and FIG. 16). Then, using a E/T ratio of 50/1, 20/1 and 8/1, ADCC activity against CHO cells was compared (FIG. 17 and FIG. 18).

As a result, at any E/T ratio, ADCC activity was induced in proportion to Log MEFL. It was also shown that even in cells in which the amount expressed of HM1.24 antigen is low, for example CHO/HM25 (the number of HM1.24 antigen is about 3,000 per cell), ADCC is induced if the concentration of humanized anti-HM1.24 antibody is increased. On the other hand, in cells in which the amount expressed of HM1.24 antigen is high, for example CHO/HM36 (the number of HM1.24 antigens is about 200,000 per cell), ADCC was induced even at a low concentration (0.01 μg/ml) of humanized anti-HM1.24 antibody. These results indicate that sensitivity to the antibody therapy can be predicted by determining the amount expressed of antigen.

Figure 19:
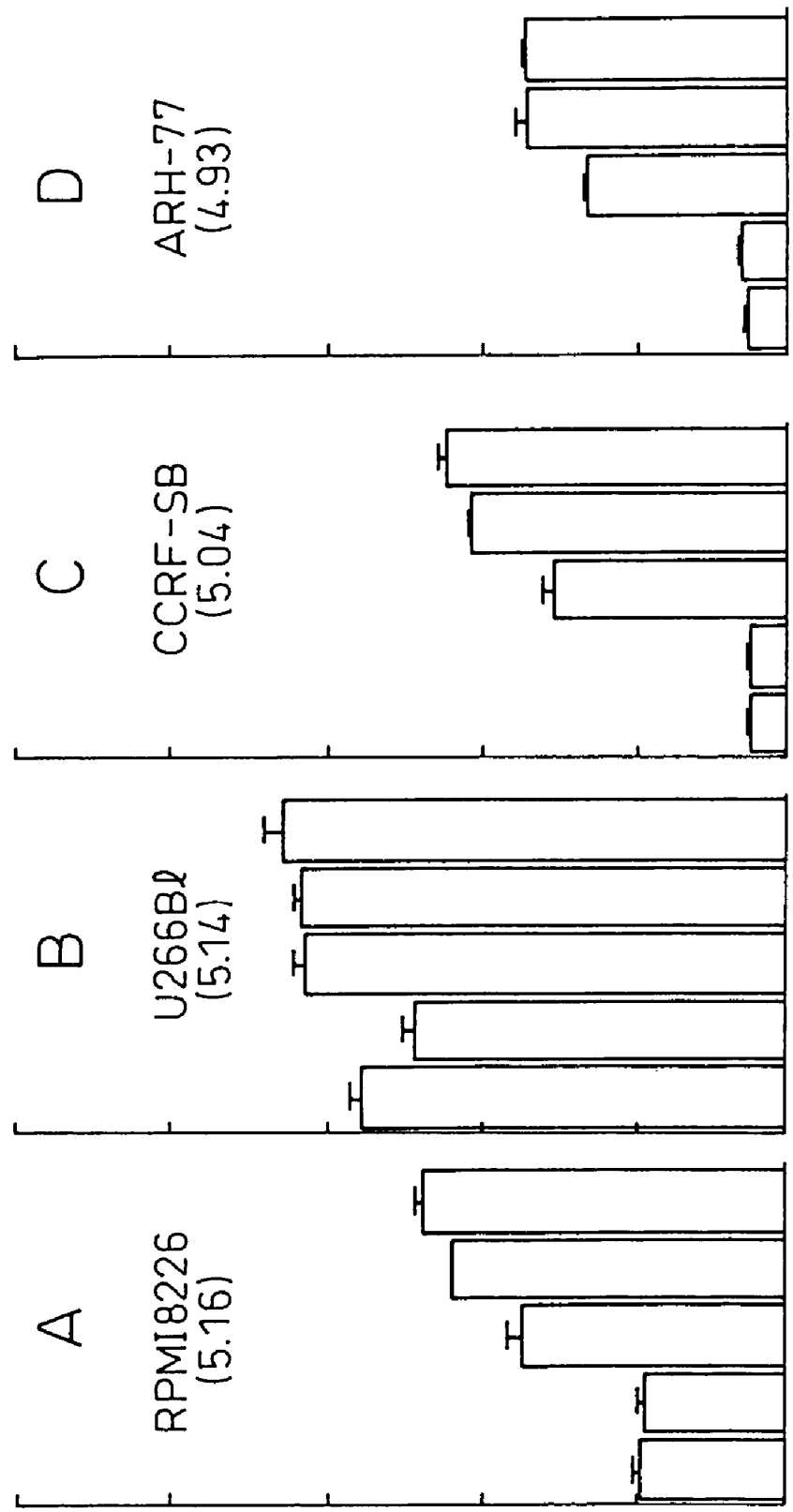
FIG. 19 is an illustration showing ADCC activity due to humanized anti-HM1.24 antibody (AHM) in various cell lines.
Figure 20:
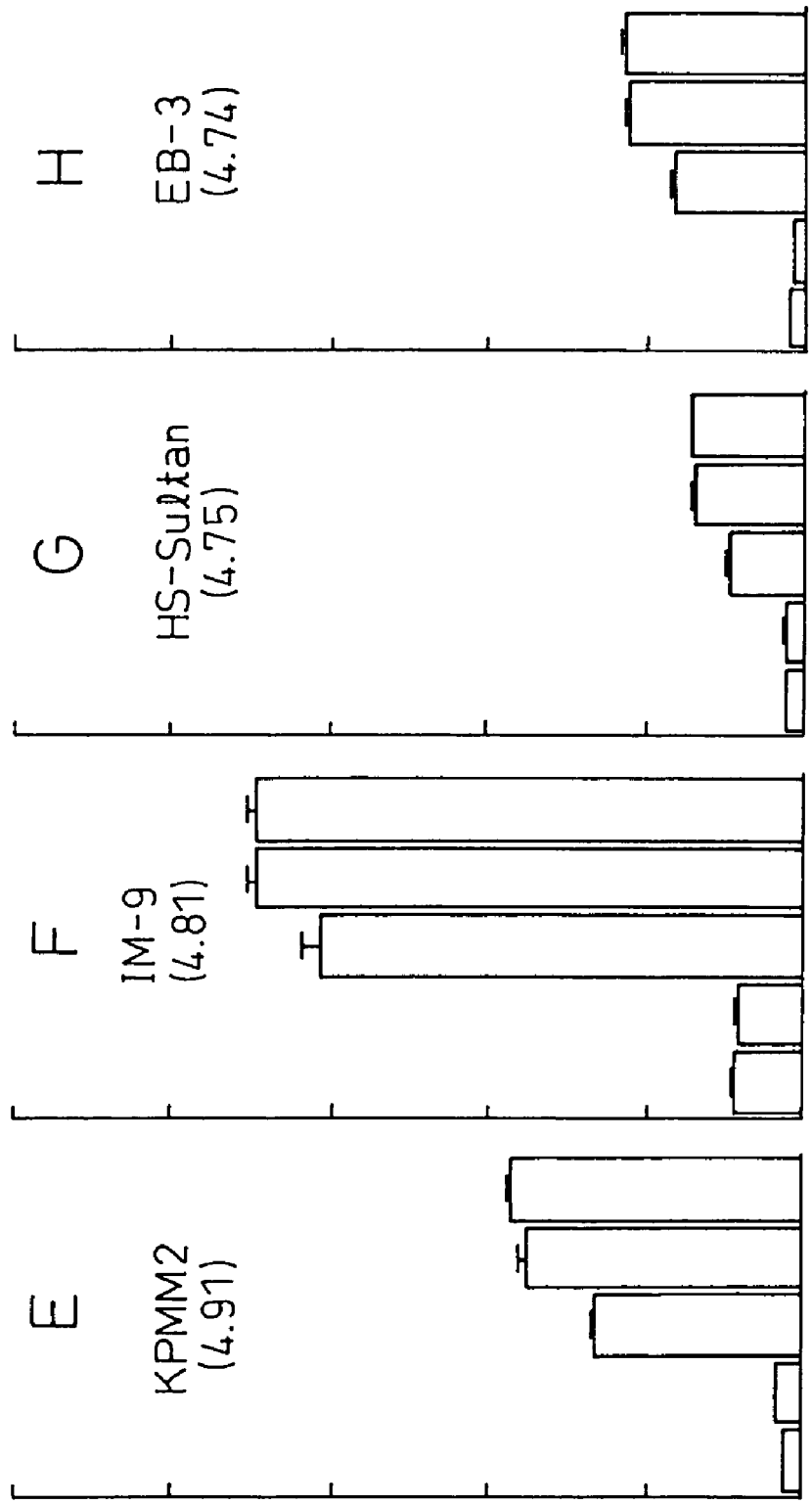
FIG. 20 is an illustration showing ADCC activity due to humanized anti-HM1.24 antibody (AHM) in various cell lines.
Figure 21:
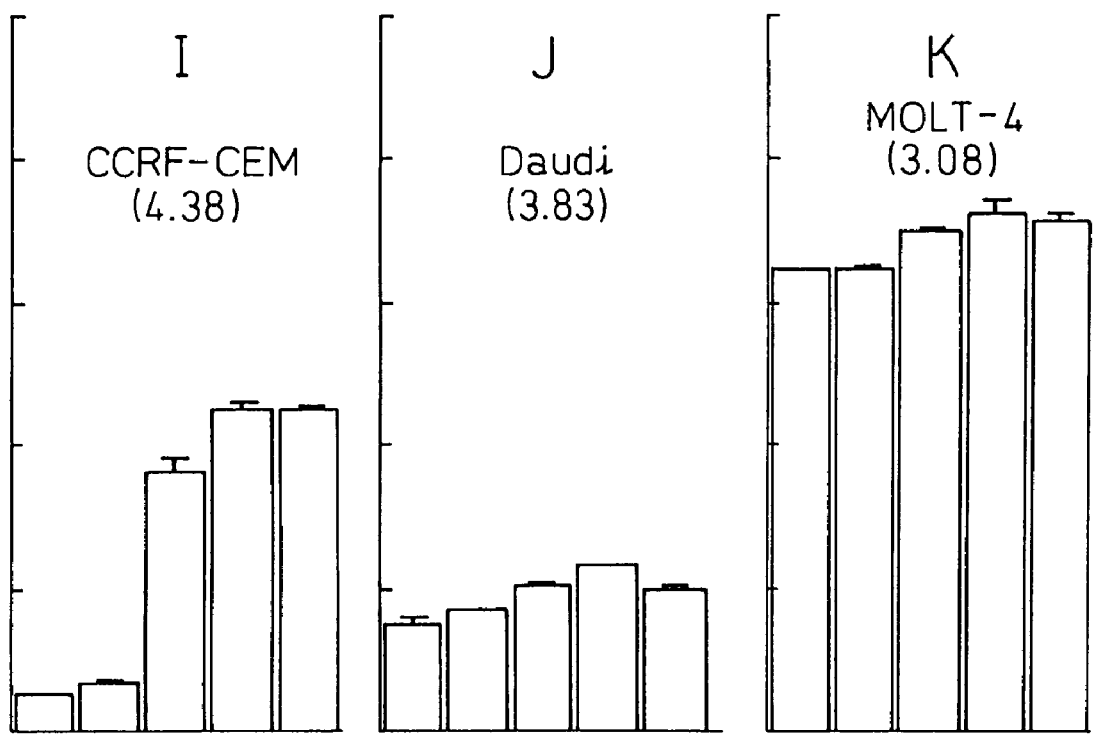
FIG. 21 is an illustration showing ADCC activity due to humanized anti-HM1.24 antibody (AHM) in various cell lines.

Furthermore, for 11 hematopoietic tumor cell lines including myeloma cells, Log MEFL and ADCC activity were determined (FIG. 19 to FIG. 21). The amounts expressed of HM1.24 antigen for cell lines were, in a decreasing order, RPMI8226 (Log MEFL: 5.16), U266B1 (5.14), CCRF-SB (5.04), ARH-77 (4.93), KPMM2 (4.91), IM-9 (4.81), HS-Sultan (4.75), EB-3 (4.74), CCRF-CEM (4.38), Daudi (3.83), and MOLT-4 (3.08). When Log MEFL values are converted to the number of HM1.24 antigens, they were $1.66 \times 10^5$, $1.59 \times 10^5$, $1.29 \times 10^5$, $1.01 \times 10^5$, $9.72 \times 10^4$, $7.84 \times 10^4$, $6.89 \times 10^4$, $6.75 \times 10^4$, $3.11 \times 10^4$, $9.53 \times 10^3$, and $1.90 \times 10^3$. Since ADCC activity was observed in all cell lines, it was indicated that the treatment of hematopoietic tumors with humanized anti-HM1.24 antibody is possible if at least $1.90 \times 10^3$ or more of HM1.24 antigens are expressed.

(5) Discussion

With respect to the amount expressed of HM1.24 antigen on the cell, the number of HM1.24 antigens was determined in a test using $^{125}$I-humanized anti-HM1.24 antibody, and correlation with Log MEFL obtained by flow cytometry was investigated, with a result that a high correlation between the two was observed. If Log MEFL is set as x, then the number of HM1.24 antigens is expressed by $$2.53e^{2.15x}$$

and was formulated by an equation of correlation. Using this equation of correlation, the amount expressed of HM1.24 antigen can be easily quantitated by flow cytometry. Log MEFL of tumor cells derived from myeloma patients were 4.69, 4.51, 4.22, 4.11, and 3.98, which may be converted to the number of HM1.24 antigens to be $6.06 \times 10^4$, $4.11 \times 10^4$, $2.21 \times 10^4$, $1.74 \times 10^4$, and $1.32 \times 10^4$, suggesting that at least 10,000 HM1.24 antigens are present in tumor cells derived from myeloma patients.

When the ADCC activity of humanized anti-HM1.24 antibody via human PBMC was determined with HM1.24 antigen-expressing CHO cells as the target cells, there was high correlation observed between ADCC activity and Log MEFL at a humanized anti-HM1.24 antibody concentration of 10 µg/ml, 1 µg/ml, and 0.1 µg/ml. Furthermore, in any of the cells, ADCC activity was induced corresponding to the concentration of humanized anti-HM1.24 antibody and the E/T ratio. Even in CHO cells (CHO/HM25) in which the amount expressed of HM1.24 antigens per cell is about 3000, ADCC was observed when the concentration of humanized anti-HM1.24 antibody and the E/T ratio are high.

In the case of tumor cells derived from myeloma patients, the Log MEFL is about 4-4.7, and estimating from FIG. 15, when a blood concentration of humanized anti-HM1.24 antibody of 0.1 µg/ml or more is attained, ADCC can be induced, and treatment of myeloma is possible.

The invention claimed is:

1. A method for determining the equation of correlation between the number of molecules of an antigen per cell expressed on the surface of the cell, and fluorescence intensity associated with binding of a fluorescently-labeled antibody against the antigen, comprising the steps of:
  (a) preparing a plurality of cell groups comprising at least a first and a second cell group, each cell group comprising a single type of cell which expresses the antigen and for which the number of molecules of the antigen per cell expressed on the surface of the cell has been previously quantitated, wherein the number of molecules of the antigen per cell expressed on the surface of the cell in a first cell group differs from the amount in at least the second cell group;
  (b) preparing a fluorescence-labeled antibody having a known titer that specifically binds to the antigen;
  (c) individually contacting each cell group of (a) with the fluorescence-labeled antibody of (b);
  (d) determining the fluorescence intensity of the antibody bound to the antigen on the surface of the cell for each of the cell groups of (a); and
  (e) analyzing the correlation between the number of molecules of the antigen per cell expressed on the surface of the cell and each of the fluorescence intensity measurements determined in (d).

2. The method according to claim 1 wherein the step of preparing a plurality of cell groups for which the number of molecules of the antigen per cell expressed on the surface of the cell has previously been quantitated comprises the step of quantitating the amount expressed of said antigen using an antibody labelled with a radioisotope.

3. The method according to claim 2 wherein said plurality of cell groups are cell groups for which the number of molecules of the antigen per cell expressed on the surface of the cell is different by at least 10-fold.

4. The method according to claim 1 wherein said antigen is specifically expressed on the surface of cancer cells.

5. The method according to claim 4 wherein said antigen is HM1.24 antigen set forth in SEQ ID NO: 1.

6. The method according to any one of claims 1 to 3 wherein the antibody has antibody-dependent cellular cytotoxicity (ADCC) activity and/or a complement-dependent cytotoxicity (CDC) activity.

7. The method according to any one of claims 1 to 3 wherein the antibody is labelled with fluorescein.

8. The method according to any one of claims 1 to 3 wherein the antibody is anti-HM1.24 antibody.

9. The method according to claim 8 wherein the anti-HM1.24 antibody is humanized.

10. The method according to any one of claims 1 to 3 wherein the step of determining fluorescence intensity is performed using flow cytometry.

11. The method according to any one of claims 1 to 3 wherein the equation of correlation between fluorescence intensity and the number of molecules of the antigen per cell expressed on the surface of the cell is expressed by the number of antigens$=2.53e^{3.15 Log\ MEFL}$, wherein MEFL is the number of molecules of equivalent fluorescence.

* * * * *

SEQUENCE LISTING

<160> NUMBER OF SEQ ID NOS: 6

<210> SEQ ID NO 1
<211> LENGTH: 1013
<212> TYPE: DNA
<213> ORGANISM: Artificial Sequence
<220> FEATURE:
<223> OTHER INFORMATION: Nucleotide sequence coding for HM 1.24 antigen

<400> SEQUENCE: 1

```
gaattcggca cgagggatct gg atg gca tct act tcg tat gac tat tgc          49
                         Met Ala Ser Thr Ser Tyr Asp Tyr Cys
                          1               5 aga gtg ccc atg gaa gac ggg gat aag cgc tgt aag ctt ctg ctg ggg        97
Arg Val Pro Met Glu Asp Gly Asp Lys Arg Cys Lys Leu Leu Leu Gly
 10              15                  20                  25 ata gga att ctg gtg ctc ctg atc atc gtg att ctg ggg gtg ccc ttg       145
Ile Gly Ile Leu Val Leu Leu Ile Ile Val Ile Leu Gly Val Pro Leu
             30                  35                  40 att atc ttc acc atc aag gcc aac agc gag gcc tgc cgg gac ggc ctt       193
Ile Ile Phe Thr Ile Lys Ala Asn Ser Glu Ala Cys Arg Asp Gly Leu
         45                  50                  55 cgg gca gtg atg gag tgt cgc aat gtc acc cat ctc ctg caa caa gag       241
Arg Ala Val Met Glu Cys Arg Asn Val Thr His Leu Leu Gln Gln Glu
     60                  65                  70 ctg acc gag gcc cag aag ggc ttt cag gat gtg gag gcc cag gcc gcc       289
Leu Thr Glu Ala Gln Lys Gly Phe Gln Asp Val Glu Ala Gln Ala Ala
 75                  80                  85 acc tgc aac cac act gtg atg gcc cta atg gct tcc ctg gat gca gag       337
Thr Cys Asn His Thr Val Met Ala Leu Met Ala Ser Leu Asp Ala Glu
 90                  95                 100                 105 aag gcc caa gga caa aag aaa gtg gag gag ctt gag gga gag atc act       385
Lys Ala Gln Gly Gln Lys Lys Val Glu Glu Leu Glu Gly Glu Ile Thr
             110                 115                 120
```

```
aca tta aac cat aag ctt cag gac gcg tct gca gag gtg gag cga ctg         433
Thr Leu Asn His Lys Leu Gln Asp Ala Ser Ala Glu Val Glu Arg Leu
            125                 130                 135 aga aga gaa aac cag gtc tta agc gtg aga atc gcg gac aag aag tac         481
Arg Arg Glu Asn Gln Val Leu Ser Val Arg Ile Ala Asp Lys Lys Tyr
        140                 145                 150 tac ccc agc tcc cag gac tcc agc tcc gct gcg gcg ccc cag ctg ctg         529
Tyr Pro Ser Ser Gln Asp Ser Ser Ser Ala Ala Ala Pro Gln Leu Leu
    155                 160                 165 att gtg ctg ctg ggc ctc agc gct ctg ctg cag tga gatcccagga              575
Ile Val Leu Leu Gly Leu Ser Ala Leu Leu Gln ***
170             175                 180 agctggcaca tcttggaagg tccgtcctgc tcggcttttc gcttgaacat tcccttgatc       635
tcatcagttc tgagcgggtc atggggcaac acggttagcg gggagagcac ggggtagccg       695
gagaagggcc tctggagcag gtctggaggg gccatggggc agtcctgggt ctggggacac       755
agtcgggttg acccagggct gtctccctcc agagcctccc tccggacaat gagtcccccc       815
tcttgtctcc caccctgaga ttgggcatgg ggtgcggtgt gggggggcatg tgctgcctgt      875 tgttatgggt ttttttttgcg gggggggttg ctttttttctg gggtctttga gctccaaaaa    935
aataaacact tcctttgagg gagagcacac cttaaaaaaa aaaaaaaaaa aaaaaaaaa        995 aaaattcggg cggccgcc                                                    1013

<210> SEQ ID NO 2
<211> LENGTH: 180
<212> TYPE: PRT
<213> ORGANISM: Homo sapiens
<220> FEATURE:
<223> OTHER INFORMATION: Amino acid sequence of HM 1.24 antigen

<400> SEQUENCE: 2

Met Ala Ser Thr Ser Tyr Asp Tyr Cys Arg Val Pro Met Glu Asp Gly
  1               5                  10                  15

Asp Lys Arg Cys Lys Leu Leu Leu Gly Ile Gly Ile Leu Val Leu Leu
                 20                  25                  30

Ile Ile Val Ile Leu Gly Val Pro Leu Ile Ile Phe Thr Ile Lys Ala
             35                  40                  45

Asn Ser Glu Ala Cys Arg Asp Gly Leu Arg Ala Val Met Glu Cys Arg
         50                  55                  60

Asn Val Thr His Leu Leu Gln Gln Glu Leu Thr Glu Ala Gln Lys Gly
 65                  70                  75                  80

Phe Gln Asp Val Glu Ala Gln Ala Ala Thr Cys Asn His Thr Val Met
                 85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180
```

<210> SEQ ID NO 3
<211> LENGTH: 379
<212> TYPE: DNA
<213> ORGANISM: Artificial Sequence
<220> FEATURE:
<223> OTHER INFORMATION: Nucleotide sequence coding for reshaped human
      anti-HM 1.24 antibody L chain V region version a

<400> SEQUENCE: 3

```
atg gga tgg agc tgt atc atc ctc tcc ttg gta gca aca gct aca ggt        48
Met Gly Trp Ser Cys Ile Ile Leu Ser Leu Val Ala Thr Ala Thr Gly
            -15                 -10                 -5 gtc cac tcc gac atc cag atg acc cag agc cca agc agc ctg agc gcc        96
Val His Ser Asp Ile Gln Met Thr Gln Ser Pro Ser Ser Leu Ser Ala
        -1   1               5                   10 agc gtg ggt gac aga gtg acc atc acc tgt aag gct agt cag gat gtg       144
Ser Val Gly Asp Arg Val Thr Ile Thr Cys Lys Ala Ser Gln Asp Val
     15                  20                  25 aat act gct gta gcc tgg tac cag cag aag cca gga aag gct cca aag       192
Asn Thr Ala Val Ala Trp Tyr Gln Gln Lys Pro Gly Lys Ala Pro Lys
 30                  35                  40                  45 ctg ctg atc tac tcg gca tcc aac cgg tac act ggt gtg cca agc aga       240
Leu Leu Ile Tyr Ser Ala Ser Asn Arg Tyr Thr Gly Val Pro Ser Arg
             50                  55                  60 ttc agc ggt agc ggt agc ggt acc gac ttc acc ttc acc atc agc agc       288
Phe Ser Gly Ser Gly Ser Gly Thr Asp Phe Thr Phe Thr Ile Ser Ser
         65                  70                  75 ctc cag cca gag gac atc gct acc tac tac tgc cag caa cat tat agt       336
Leu Gln Pro Glu Asp Ile Ala Thr Tyr Tyr Cys Gln Gln His Tyr Ser
     80                  85                  90 act cca ttc acg ttc ggc caa ggg acc aag gtg gaa atc aaa c             379
Thr Pro Phe Thr Phe Gly Gln Gly Thr Lys Val Glu Ile Lys
 95                 100                 105
```

<210> SEQ ID NO 4
<211> LENGTH: 126
<212> TYPE: PRT
<213> ORGANISM: Artificial Sequence
<220> FEATURE:
<221> NAME/KEY:
<222> LOCATION:
<223> OTHER INFORMATION: Amino acid sequence of reshaped human
      anti-HM1.24 antibody L chain V region version a

<400> SEQUENCE: 4

```
Met Gly Trp Ser Cys Ile Ile Leu Ser Leu Val Ala Thr Ala Thr Gly
            -15                 -10                 -5

Val His Ser Asp Ile Gln Met Thr Gln Ser Pro Ser Ser Leu Ser Ala
        -1   1               5                   10

Ser Val Gly Asp Arg Val Thr Ile Thr Cys Lys Ala Ser Gln Asp Val
     15                  20                  25

Asn Thr Ala Val Ala Trp Tyr Gln Gln Lys Pro Gly Lys Ala Pro Lys
 30                  35                  40                  45

Leu Leu Ile Tyr Ser Ala Ser Asn Arg Tyr Thr Gly Val Pro Ser Arg
             50                  55                  60

Phe Ser Gly Ser Gly Ser Gly Thr Asp Phe Thr Phe Thr Ile Ser Ser
         65                  70                  75

Leu Gln Pro Glu Asp Ile Ala Thr Tyr Tyr Cys Gln Gln His Tyr Ser
     80                  85                  90

Thr Pro Phe Thr Phe Gly Gln Gly Thr Lys Val Glu Ile Lys
 95                 100                 105
```

```
<210> SEQ ID NO 5
<211> LENGTH: 418
<212> TYPE: DNA
<213> ORGANISM: Artificial Sequence
<220> FEATURE:
<223> OTHER INFORMATION: Nucleotide sequence coding for reshaped human
      anti-HM 1.24 antibody H chain V region version s

<400> SEQUENCE: 5 atg gac tgg acc tgg agg gtc ttc ttc ttg ctg gct gta gct cca ggt        48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag        96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc       144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt       192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt       240
Glu Trp Met Gly Ser Ile Phe Pro Gly Asp Gly Asp Thr Arg Tyr Ser
                 50                  55                  60 cag aag ttc aag ggc aga gtc acc atc acc gca gac aag tcc acg agc       288
Gln Lys Phe Lys Gly Arg Val Thr Ile Thr Ala Asp Lys Ser Thr Ser
                 65                  70                  75 aca gcc tac atg gag ctg agc agc ctg aga tct gag gac acg gcc gtg       336
Thr Ala Tyr Met Glu Leu Ser Ser Leu Arg Ser Glu Asp Thr Ala Val
             80                  85                  90 tat tac tgt gcg aga gga tta cga cga ggg ggg tac tac ttt gac tac       384
Tyr Tyr Cys Ala Arg Gly Leu Arg Arg Gly Gly Tyr Tyr Phe Asp Tyr
         95                 100                 105 tgg ggg caa ggg acc acg gtc acc gtc tcc tca g                         418
Trp Gly Gln Gly Thr Thr Val Thr Val Ser Ser
110                 115                 120

<210> SEQ ID NO 6
<211> LENGTH: 139
<212> TYPE: PRT
<213> ORGANISM: Artificial Sequence
<220> FEATURE:
<221> NAME/KEY:
<222> LOCATION:
<223> OTHER INFORMATION: Amino acid sequence of reshaped human anti-HM
      1.24 antibody H chain V region version s

<400> SEQUENCE: 6

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
         -1   1                   5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Arg Val Thr Ile Thr Ala Asp Lys Ser Thr Ser
                 65                  70                  75

Thr Ala Tyr Met Glu Leu Ser Ser Leu Arg Ser Glu Asp Thr Ala Val
```

-continued

```
                80                     85                       90
Tyr Tyr Cys Ala Arg Gly Leu Arg Arg Gly Gly Tyr Tyr Phe Asp Tyr
         95                    100                    105

Trp Gly Gln Gly Thr Thr Val Thr Val Ser Ser
110                 115                 120
```